(12) United States Patent
Lin et al.

(10) Patent No.: US 9,400,233 B2
(45) Date of Patent: Jul. 26, 2016

(54) SENSORS FOR LONG-TERM AND CONTINUOUS MONITORING OF BIOCHEMICALS

(75) Inventors: Qiao Lin, New York, NY (US); Xian Huang, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 13/246,404

(22) Filed: Sep. 27, 2011

(65) Prior Publication Data
US 2012/0043203 A1 Feb. 23, 2012

Related U.S. Application Data

(63) Continuation of application No. PCT/US2009/062891, filed on Oct. 30, 2009.

(60) Provisional application No. 61/171,338, filed on Apr. 21, 2009, provisional application No. 61/225,473, filed on Jul. 14, 2009, provisional application No. 61/225,475, filed on Jul. 14, 2009.

(51) Int. Cl.
*G01N 33/00* (2006.01)
*G01N 1/16* (2006.01)

(52) U.S. Cl.
CPC .......................................... *G01N 1/16* (2013.01)

(58) Field of Classification Search
CPC .................................. G01N 1/16; G01N 33/00
See application file for complete search history.

(56) References Cited

U.S. PATENT DOCUMENTS

| 4,979,509 | A | 12/1990 | Hakky |
| 6,016,686 | A | 1/2000 | Thundat |
| 6,210,326 | B1 | 4/2001 | Ehwald |
| 6,397,661 | B1 | 6/2002 | Grimes et al. |
| 6,514,718 | B2 | 2/2003 | Heller et al. |
| 6,935,165 | B2 | 8/2005 | Bashir et al. |
| 7,074,637 | B2 | 7/2006 | Lutz et al. |
| 7,256,695 | B2 | 8/2007 | Hamel et al. |
| 7,287,415 | B2 | 10/2007 | Borwick, III et al. |
| 7,499,738 | B2 | 3/2009 | Gerber et al. |
| 7,704,704 | B2 | 4/2010 | Ibey et al. |

(Continued)

FOREIGN PATENT DOCUMENTS

WO WO 2010/0123521 10/2010
WO WO 2014/018688 1/2014

OTHER PUBLICATIONS

Zhao, Yongjun "A MEMS viscometric sensor for continuous glucose monitoring." J. Micromech. Microeng. 17 (2007) 2528-2537.*

(Continued)

*Primary Examiner* — Sam P Siefke
(74) *Attorney, Agent, or Firm* — Baker Botts L.L.P.

(57) ABSTRACT

The disclosed subject matter relates to a sensor or system for monitoring a target analyte by using a polymer solution that is capable of binding to the analyte. The sensor of the disclosed subject matter includes a viscosity-based sensor or a permittivity-based sensor. The viscosity-based sensor contains a semi-permeable membrane, a substrate, and a microchamber including a vibrational element. The permittivity-based sensor contains a semi-permeable membrane, a substrate, and a microchamber. The sensor discussed herein provides excellent reversibility and stability as highly desired for long-term analyte monitoring.

11 Claims, 36 Drawing Sheets

(56) References Cited

U.S. PATENT DOCUMENTS

| | | | |
|---|---|---|---|
| 7,896,809 B2 | 3/2011 | Simpson et al. | |
| 8,003,397 B2 * | 8/2011 | Wang et al. | 436/95 |
| 2004/0073100 A1 | 4/2004 | Ballerstadt et al. | |
| 2005/0262943 A1 | 12/2005 | Claydon et al. | |
| 2007/0132043 A1 | 6/2007 | Bradley et al. | |
| 2009/0191642 A1 | 7/2009 | Wang et al. | |

OTHER PUBLICATIONS

International Search Report and Written Opinion for PCT/US2012/048819, dated Nov. 15, 2012.

Huang, et al., "A MEMS Differentially Affinity Sensor for Continuous Glucose Detection", *Solid-State Sensors, Actuators and Microsystems Conference*, (Abstract only) Jun. 5-9, 2011.

Huang, et al., "A Capacitively Based MEMS Affinity Glucose Sensor", *Solid-State Sensors, Actuators and Microsystems Conference*, 2009, pp. 1457-1460 Jun. 21-25, 2009.

Huang, et al., "A MEMS Affinity Glucose Sensor Using a Biocompatible Glucose-Responsive Polymer", *Sensors and Actuators B: Chemical*, 140(2):603-609 (2009).

Huang, et al., "A Capacitative MEMS Viscometric Sensor for Affinity Detection of Glucose", *Journal of Micraelectromechanical Systems*, 18:1246-1254 (2009).

Haung, et al., A MEMS Sensor for Continuous Monitoring of Glucose in Subcutaneous Tissue:, *IEEE 22nd International Conference on Micro Electra Mechanical Systems (MEMS 2009)*, Sorrento, Italy, pp. 352-355 (2009).

Haung, et al., "A Biocompatible Affinity MEMS Sensor for Continuos Monitoring of Glucose", *IEEE 4th International Conference on Nano/Micro Engineered and Molecular Systems (NEMS 2009)*, Shenzen, China, pp. 797-802 (2009).

Mansouri, et al., "A Miniature Optical Glucose Sensor Based on Affinity Binding", *Nature Biotechnology*, 2:885-890 (1984).

International Search Report and Written Opinion for PCT/US2009/062891 dated Jan. 13, 2010.

Barnes et al., "A femtojoule calorimeter using micromechanical sensors", AIP: Review of Scientific Instruments, 65:3793-3798 (Dec. 1994).

Cavicchi et al., "Micro-differential scanning calorimeter for combustible gas sensing", Sensors and Actuators B; Chemical, 97(1):22-30 (Jan. 2004).

Lai et al., "High-speed ($10^4$ ° C/s) scanning microcalorimetry with monolayer sensitivity ($J/m^2$)", Applied Physics Letters, 67:1229-1231 (Aug. 1995).

Vanden Poel et al., "Performance and calibration of the flash DSC1, a new, MEMS-based fast scanning calorimeter", Journal of Thermal Analysis and Calorimetry, 110(3):1533-1546 (Dec. 2012).

Wang et al., "A MEMS Isothermal Titration Biocalorimeter", 16th International Conference on Miniaturized Systems for Chemistry and Life Sciences, pp. 195-197 (Oct. 28-Nov. 1, 2012) Okinawa, Japan.

\* cited by examiner

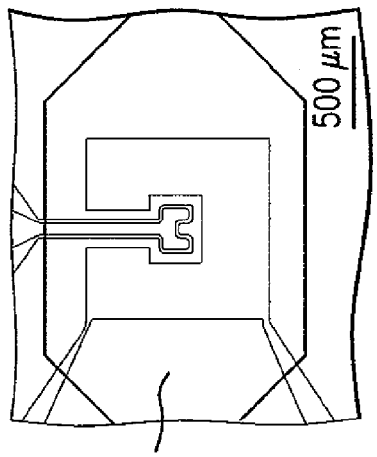
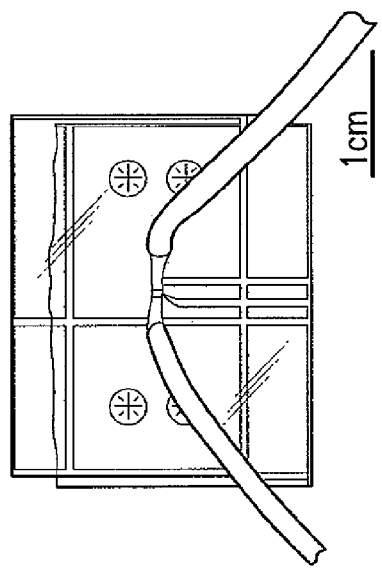
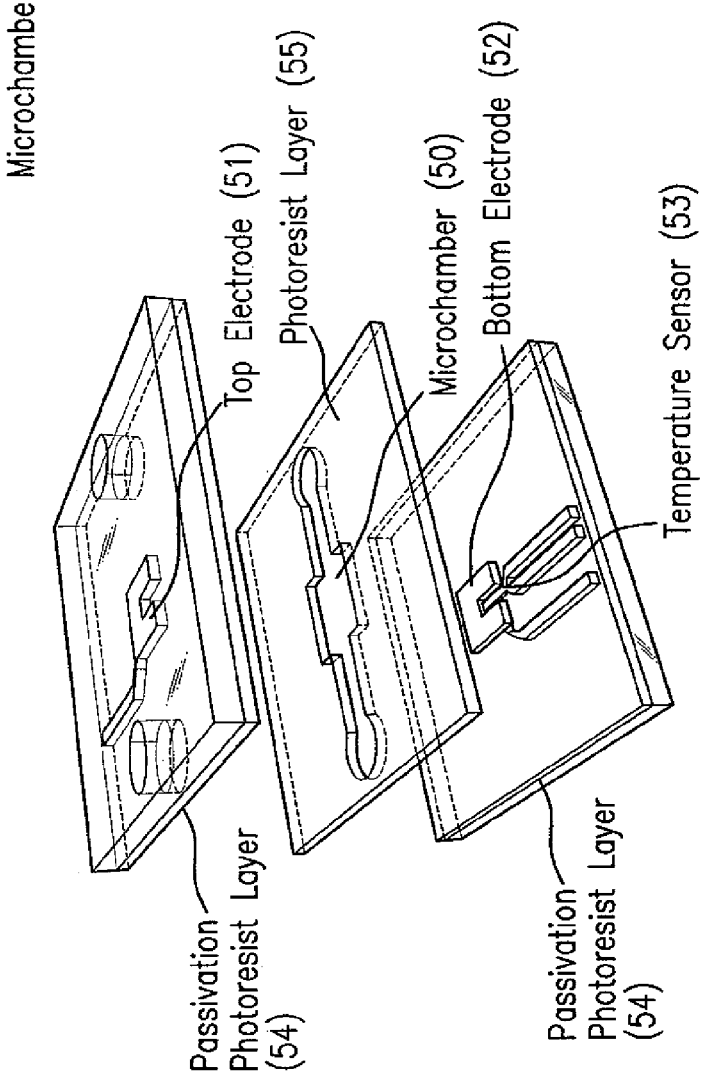
FIG. 32B
FIG. 32C
FIG. 32A
Microchamber (50)
Top Electrode (51)
Photoresist Layer (55)
Microchamber (50)
Bottom Electrode (52)
Temperature Sensor (53)
Passivation Photoresist Layer (54)
Passivation Photoresist Layer (54)

SENSORS FOR LONG-TERM AND CONTINUOUS MONITORING OF BIOCHEMICALS

CROSS REFERENCE TO RELATED APPLICATIONS

This application is a U.S. National Phase under 35 U.S.C. §371 of International Application PCT/US09/062,891, filed Oct. 30, 2009, and which claims priority to U.S. Provisional Application Nos. 61/171,338, filed on Apr. 21, 2009; 61/225,473, filed Jul. 14, 2009; and 61/225,475, filed Jul. 14, 2009, the disclosures of which are hereby incorporated by reference in their entireties.

STATEMENT REGARDING FEDERALLY SPONSORED RESEARCH OR DEVELOPMENT

This invention was made with government support under NIH grant number DK63068-05 awarded by National Institutes of Health, and NSF grant number ECCS-0702101 awarded by National Science Foundation. The United States Government has certain rights in the invention.

BACKGROUND

Diabetes mellitus is a metabolic disease characterized by persistent hyperglycemia (high blood sugar levels). Close monitoring of daily physiological glucose levels reduces the risk of complications caused by conditions such as hypoglycemia or hyperglycemia. This can be achieved by continuous glucose monitoring (CGM) systems, which involve either non-invasive or minimally invasive detection of glucose. Currently, subcutaneously implanted enzymatic electrochemical detection is a prevailing CGM technique, and is the basis for a number of commercially available sensors. These FDA approved commercial products detect glucose by enzyme-catalyzed reactions.

Electrochemical methods are sensitive and specific for glucose detection, but suffer from drawbacks. Firstly, the irreversible consumption of glucose in electrochemical detection induces a potential change in the equilibrium glucose concentration in the tissue, and thus, affects the actual measured glucose level. Furthermore, the rate of glucose consumption can be diffusion limited. Any changes in diffusion layers due to biofouling (e.g., by protein adsorption, cell deposition, and capsule formation) on the sensor surface can affect the diffusion rate, and, thus, the sensor sensitivity. In addition, drift from hydrogen peroxide production and interference from electrode-active chemicals can cause erosion of the sensor electrodes and deactivation of functional enzymes, compromising the sensor accuracy, reliability and longevity. As a result, electrochemical CGM sensors can exhibit large drifts over time, and require frequent calibration by finger pricks. This lack of reliability has been severely hindering CGM applications to practical diabetes management.

To overcome the drawbacks of electrochemical detection, alternative glucose sensing techniques have been investigated. Methods that use non-consumptive, competitive affinity binding of glucose have been considered. One technique exploits the solution of a polysaccharide (e.g., dextran) crosslinked by a glucose-binding protein (e.g., concanavalin A, or Con A): glucose binds competitively to Con A and causes reversible de-crosslinking of the dextran—Con A complex, which can be detected via the resulting changes in solution properties, such as fluorescence or viscosity. As affinity sensing is based on equilibrium binding in which glucose is not consumed, it is not susceptible to electroactive interferents. Also, affinity sensing is considerably more tolerant to biofouling. That is, the deposition of biological material (e.g., cells and proteins) on the implanted affinity sensor surface results only in an increased equilibration time without any changes in measurement accuracy. Consequently, affinity glucose sensors can be highly stable and low-drift.

Unfortunately, Con A is immunogenic and cytotoxic and degrades with time. Although certain alternatives, such as ones utilizing Microelectromechanical Systems (MEMS) technology have been developed, they can suffer from the same or different limitations associated with Con A, e.g., limited mechanical reliability, poor reversibility, and significant drifts. Thus, there remains a need in the art for a sensor for stable and potentially implantable MEMS-based continuous glucose sensing.

SUMMARY

The presently disclosed subject matter provides a sensor for monitoring a target analyte by using a polymer solution that is capable of binding to the analyte, which sensor includes a semi-permeable membrane which includes a material permeable to the analyte, a substrate, and a microchamber including a vibrational element therein, formed between the semi-permeable membrane and the substrate, and adapted to receive the polymer solution, such that when the analyte is placed on the semi-permeable membrane, at least a portion of the analyte will permeate the semi-permeable membrane and bind to at least a portion of the polymer solution to thereby cause a change in vibration of the vibrational element. In one embodiment, the change in vibration of the vibrational element of the sensor is caused by a change in viscosity of the polymer solution. In certain embodiments, the vibrational element includes a vibrational cantilever or a vibrational diaphragm. In other embodiments, the sensor further comprises a detector which is coupled to the microchamber for detecting a viscosity change, if any, caused by binding between the analyte and the polymer. The detector includes an optical lever or a capacitive detector.

In the disclosed subject matter, the polymer can reversely bind to the analyte. In certain embodiments, the analyte can be glucose. The polymer solution can include a polymer having a plurality of boronic acid moieties. In certain embodiments, the polymer includes poly(acrylamide-ran-3-acrylamidophenylboronic acid) (PAA-ran-PAAPBA).

The vibrational element of the disclosed subject matter can include Parylene. In certain embodiments, when the vibrational element is a vibrational diaphragm, the sensor further comprises a top electrode embedded in the vibrational diaphragm within the microchamber to thereby form a capacitor with a bottom electrode on the substrate. In certain embodiments, the capacitor is adapted to sense a change in the capacitance between the top electrode and the bottom electrode caused by binding between the analyte and the polymer. In other embodiments, the sensor can further comprise at least one integrated permalloy film. In certain embodiments, the permalloy film further comprises a Parylene layer for passivation.

The presently disclosed subject matter also provides a sensor for monitoring a target analyte by using a polymer solution that is capable of binding to the analyte, which sensor comprises a semi-permeable membrane comprising a material permeable to the analyte, a substrate, and a microchamber which is formed between the semi-permeable membrane and the substrate, and adapted to receive the polymer solution, such that when the analyte is placed on the semi-permeable membrane, at least a portion of the analyte will permeate the semi-permeable membrane and bind to at least a portion of the polymer solution to thereby cause a change in permittivity of the polymer solution.

In certain embodiments, the sensor further comprises a top electrode and a bottom electrode, each coupled to the microchamber. In certain embodiments, the microchamber comprises the gap between the top electrode and the bottom electrode. In other embodiments, the sensor further comprises a detector which is coupled to the microchamber, for detecting a permittivity change, if any, caused by binding between the analyte and the polymer. The detector includes a capacitance-voltage transformation circuit. In other embodiments, the sensor further comprises a temperature sensor.

BRIEF DESCRIPTION OF THE DRAWINGS

FIGS. 32A-C are diagrams of a MEMS device for demonstration of dielectric affinity biosensing: (a) design schematic; and images of a fabricated device (b) before, and (c) after packaging.

DETAILED DESCRIPTION

Figure 1:
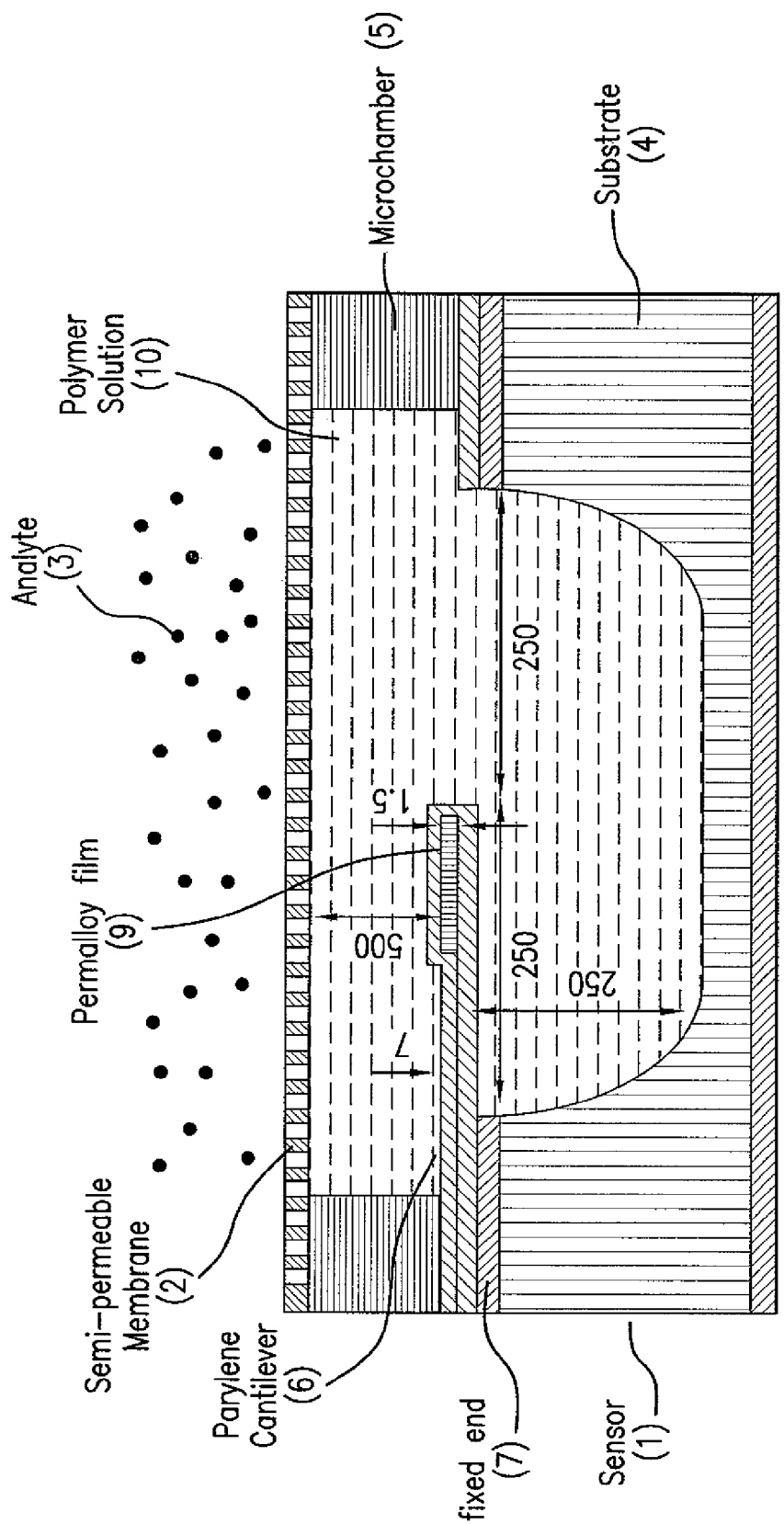
FIG. 1 is a diagram illustrating a MEMS affinity CGM sensor design in accordance with the disclosed subject matter.
Figure 2A:
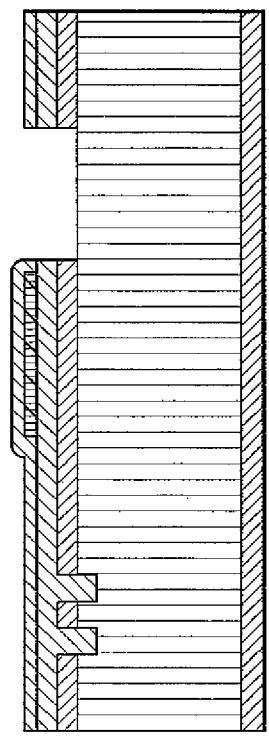
FIGS. 2A-D are diagrams illustrating a fabrication process in accordance with the disclosed subject matter: (A) etching small anchoring cavities in silicon and depositing a Parylene layer; (B) electroplating permalloy and passivating it with Parylene; (C) patterning the Parylene and permalloy layers to define a cantilever; and (D) etching silicon and $SiO_2$ to release the cantilever.
Figure 2B:
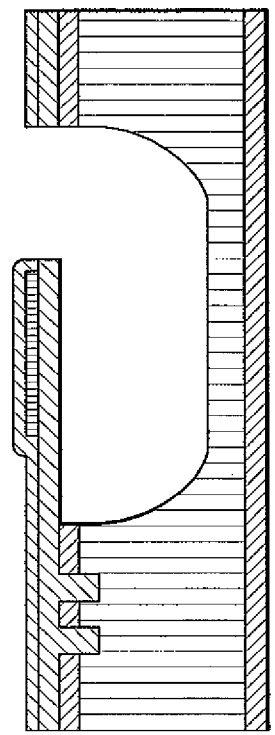
Figure 2C:
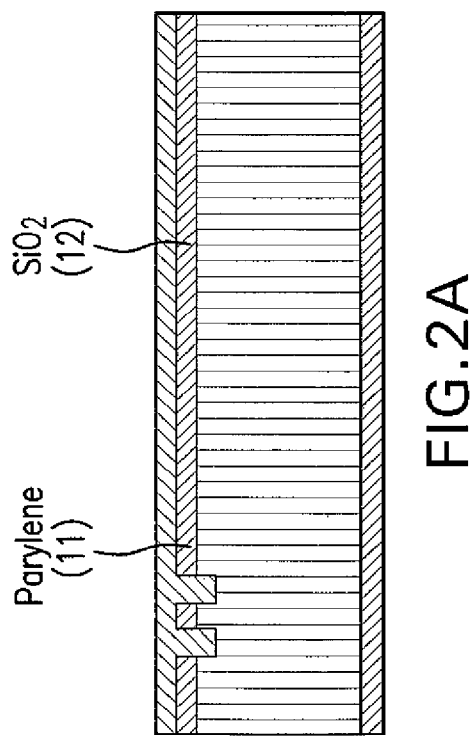
Figure 2D:
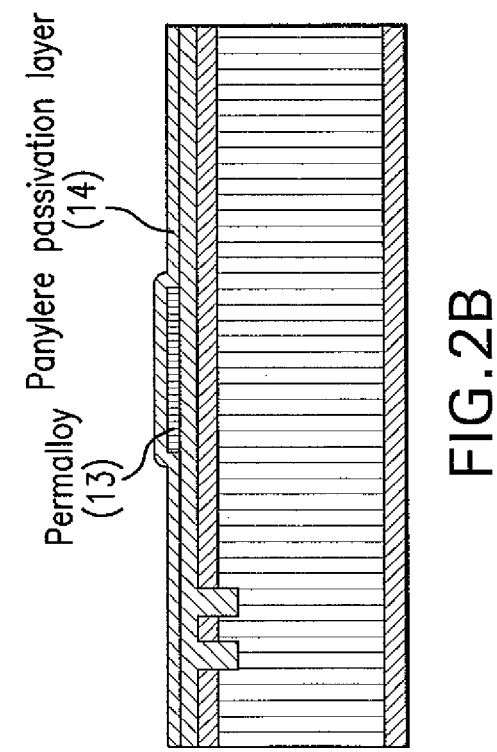

The disclosed subject matter addresses the need in the art for a stable and implantable sensor that is capable of monitoring target analytes. More specifically, the disclosed subject matter provides for a sensor and system that can be used for continuous analyte monitoring. In certain embodiments, the sensor is used for continuous glucose monitoring (CGM).

The sensor of the presently disclosed subject matter includes a sensor that can be a viscosity-based sensor or a permittivity-based sensor. The viscosity-based sensor includes a semi-permeable membrane permeable to a target analyte, a substrate, and a microchamber formed between the membrane and substrate and is adapted to receive a polymer solution. The microchamber includes a vibrational element, which can be a vibrational cantilever or a diaphragm-based sensor. In the viscosity-based sensor, the binding between the analyte of interest and the polymer can produce a viscosity change of the polymer which can be detected and measured.

The permittivity-based sensor includes a semi-permeable membrane permeable to a target analyte, a substrate, and a microchamber formed between the membrane and the substrate and is adapted to receive a polymer solution. In the permittivity-based sensor, the binding between the analyte of interest and the polymer can produce a change in the permittivity of the polymer which can be detected and measured. The sensor can then be used to monitor and detect target analytes of interest in a stable and accurate manner. Such methods can be useful in patient monitoring, diagnosis, and treatment.

Unless otherwise defined, all technical and scientific terms used herein have the same meanings as commonly understood by one of ordinary skill in the art to which the disclosed subject matter belongs. Although methods and materials similar or equivalent to those described herein can be used in its practice, suitable methods and materials are described below.

It is to be noted that the term "a" entity or "an" entity refers to one or more of that entity. As such, the terms "a", "an", "one or more", and "at least one" can be used interchangeably herein. The terms "comprising," "including," and "having" can also be used interchangeably. In addition, the terms "amount" and "level" are also interchangeable and can be used to describe a concentration or a specific quantity. Furthermore, the term "selected from the group consisting of" refers to one or more members of the group in the list that follows, including mixtures (i.e. combinations) of two or more members.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to +/−20%, up to +/−10%, up to +/−5%, or alternatively up to +/−1% of a given value. Alternatively, with respect to biological systems or processes, the term can mean within an order of magnitude, preferably within 5-fold, and more preferably within 2-fold, of a value.

As used herein, the term "analyte" is a broad term and is used in its ordinary sense and includes, without limitation, any chemical species the presence or concentration of which is sought in material sample by the sensors and systems disclosed herein. For example, the analyte(s) include, but not are limited to, glucose, ethanol, insulin, water, carbon dioxide, blood oxygen, cholesterol, bilirubin, ketones, fatty acids, lipoproteins, albumin, urea, creatinine, white blood cells, red blood cells, hemoglobin, oxygenated hemoglobin, carboxyhemoglobin, organic molecules, inorganic molecules, pharmaceuticals, cytochrome, various proteins and chromophores, microcalcifications, electrolytes, sodium, potassium, chloride, bicarbonate, and hormones. In one embodiment, the analyte is glucose. In various embodiments, the analytes can be other metabolites, such as lactate, fatty acids, cysteines and homocysteines.

As used herein, "response time" or "time constant" represents time consumption for analyte permeation into the microchamber and equilibrium binding with the polymer. Response time is time for a sensor to complete one measurement cycle. The response time of current commercial CGM products is between about 5 and about 15 minutes. In various embodiments of the disclosed subject matter, the response times of the sensor are less than about 5 minutes, alternatively less than about 3 minutes, and alternatively less tan about 1.5 minutes. In certain embodiments, the response times are about 1.5 minutes or about 3 minutes.

As used herein, the term "vibrational element" refers to a mechanical moving part, which is capable of vibrating. The vibrational element as used in presently disclosed subject matter includes, but is not limited to, a vibrational cantilever or a vibrational diaphragm.

The Sensor

The disclosed subject matter provides a sensor for monitoring a target analyte by using a polymer solution that is capable of binding to the analyte. The sensor includes a semi-permeable membrane that is made of materials permeable to the analyte, a substrate, and a microchamber. The substrate can be comprised of known applicable materials in the art including but not limited to silicone. The microchamber is formed between the semi-permeable membrane and the substrate. The analyte can permeate the membrane and bind to at least a portion of the polymer solution.

The sensor can be either a viscosity-based sensor or can be a permittivity-based sensor. When the sensor is a viscosity-based sensor, the microchamber can include either a vibrational cantilever or a vibrational diaphragm.

Viscosity-Based Sensor—Vibrational Cantilever

Figure 3A:
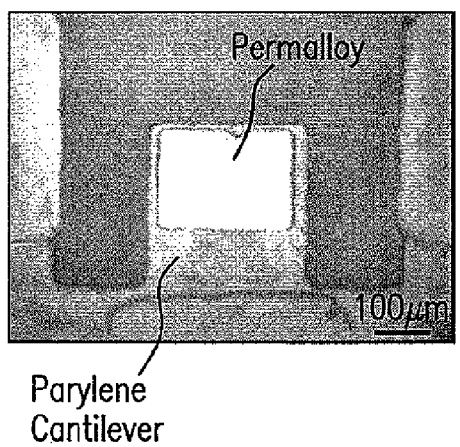
FIGS. 3A-B illustrate an exemplary fabricated MEMS CGM sensor; (A) before, and (B) after packaging.

In certain embodiments, the sensor is a viscosity-based sensor that includes a vibrational cantilever, which is also referred as "cantilever-based sensor." In these embodiments, the cantilever can be made of any appropriate polymer known in the art, including but not limited to the polymer Parylene. The cantilever is situated inside a microchamber as shown in FIGS. 1 and 3A. The microchamber is formed between a cavity etched into the substrate and a semi-permeable membrane, and is filled with a solution of polymer, for example, PAA-ran-PAAPBA. The semi-permeable membrane is made of material capable of being permeable to the target analyte. Such materials include but are not limited to cellulose acetate (CA).

The Parylene cantilever is anchored onto the substrate at one end, with its free end coated with a permalloy thin film, which is protected by an additional Parylene layer to prevent the permalloy from corrosion by the polymer solution. The environmental analyte can permeate through the semi-permeable membrane and bind with the polymer inside the microchamber. The semi-permeable membrane prevents the polymer from escaping, while allowing the analyte to diffuse into and out of the microchamber. While not part of the sensor, a test cell can be incorporated on the other side of the membrane for introduction of an analyte solution for sensor characterization. The cross-linking between the analyte and the polymer can increase the viscosity of the polymer in the microchamber as well as the damping of the cantilever vibration, causing a decrease in cantilever vibration amplitude and a shift in vibration phase which can be and detected and measured, for example, by using an optical lever technique.

As shown in FIG. 1, a cantilever-based sensor 1 includes a semi-permeable membrane 2 which is permeable to a sample analyte 3, a substrate 4, and a microchamber 5 which includes a Parylene cantilever 6. The cantilever 6 has a fixed end 7 and a free end 8. The cantilever 6 is anchored to the microchamber 5 at its fixed end 7, and its free end 8 is coated with a permalloy film 9. The permalloy film 9 is passivated by a Parylene layer. The microchamber 5 is filled with a solution of a biocompatible polymer 10 that binds with the analyte 3. The polymer includes, but is not limited to a polymer having a plurality of boronic acid moieties, for example, PAA-ran-PAAPBA. The semi-permeable membrane 2 which prevents the polymer 10 from escaping, while allowing the analyte 3 to diffuse into and out of the microchamber 5.

The sensor is placed in two mutually orthogonal magnetic fields. When the sensor is oriented horizontally, these include a vertical electromagnetic (EM) field generated by a solenoid and a horizontal magnetic field from a permanent magnet (PM). The PM magnetizes the permalloy thin film, exciting a magnetic field in the permalloy film along the cantilever length. A torque thus is generated on this magnetized permalloy film attempting to align the cantilever with the EM field. This torque is distributed along the length of the cantilever, with a magnitude proportional to the product of the permalloy volume, the EM field intensity, and the magnetization of the permalloy, and causes the cantilever to bend. Thus, a time-dependent EM field produces a time-dependent torque, resulting in vibration of the cantilever. In addition, the vibration-induced flow of the polymer solution in general imparts hydrodynamic inertia and damping on the cantilever. Because of the direct dependency of the flow-structure interaction on the viscosity of the polymer, the viscosity of the polymer can be obtained by measuring the vibration of the cantilever, allowing monitoring the presence and property of the analyte, for example, the concentration of the analyte.

The response time or time constant of the diffusion can be measured using methods known in the art, including but not limited to an estimate based on consideration of the diffusion of the analyte into the sensor. In one embodiment, the timescale for the analytes to diffuse through the semi-permeable membrane and the microchamber can be estimated to be $$t_{dif} \sim (d_m^2/\lambda + d_f^2)/D_g \quad (1)$$

where $D_g$ is the diffusivity of the analyte in the polymer solution, $d_m$ and $\lambda$ are respectively the thickness and porosity of the semi-permeable membrane, and $d_f$ is the effective height of the microchamber accounting for the deflection of the membrane caused by sample loading in the test cell. In one embodiment, the analyte is glucose, and the polymer is PAA-ran-PAAPBA. It is estimated that $D_g$ is on the order of $3 \times 10^{-11}$ m/s$^2$ according to glucose diffusivity in water ($7.1 \times 10^{10}$ m/s$^2$) scaled by the ratio of water viscosity to the viscosity of the PAA-ran-PAAPBA solution at relevant glucose concentrations. The estimator $d_m$ is approximately 20 µm, and $\lambda$ is approximately 0.6 ("Cellulose Acetate Membrane Filters," http://www.advantecmfs.com/filtration/membranes/mb-_ca.shtml), and $d_f$ is approximately 100 µM. The estimated diffusion timescale can be approximately 6 minutes.

Figure 3B:
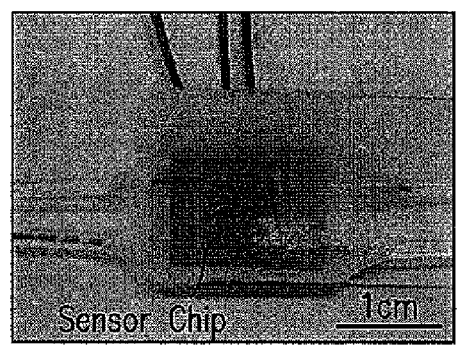

FIG. 2 illustrates an exemplary manufacturing process for the cantilever-based sensor. A Parylene layer (5 µm) 11 is deposited by chemical vapor deposition onto a SiO$_2$-coated silicon wafer 12 into which small cavities are etched (see FIG. 2A). The small cavities allow the Parylene to be anchored over an increased surface area for improved adhesion. A 100 nm copper seed layer is then deposited on the Parylene, followed by the deposition and patterning a 1.5 µm photoresist layer defining the permalloy deposition area (150 µm long and 200 µm wide). A permalloy thin film 13 is then deposited by electroplating, followed by the removal of the photoresist and unused copper, and the deposition of a second Parylene layer for passivation, therefore is referred as Parylene passivation layer 14 (2 µm) (see FIG. 2B). The two Parylene layers 11 and 14, along with the underlying SiO$_2$ layer 12, are then patterned to define a cantilever (250 µm in both length and width) (see FIG. 2C). The cantilever is finally released by gas-phase XeF$_2$ etching of the silicon underneath (forming a cavity approximately 500 µm×500 µm×250 µm in dimensions) and removal of the SiO$_2$ directly beneath the cantilever (see FIG. 2D). Following wafer dicing, a chip bonds to a poly(dimethylsiloxane) (PDMS) sheet in which a hole is fabricated by replica molding to define a microchamber with inlet and outlet channels (approximate 30 µL in dimensions), which is in turn bonded to a semi-permeable membrane (regenerated CA, with a molecular weight cutoff of 3500 Da; Fisher Scientific) using an adhesive (Devcon epoxy adhesive). Another PDMS sheet, in which a test cell (for example, in a volume of 500 µL) is fabricated along with inlet and outlet channels and wells for introduction of glucose solution, is finally adhesive bonded to the CA membrane. A fabricated cantilever-based sensor is shown in FIG. 3.

Viscosity-Based Sensor—Vibrational Diaphragm

Figure 12A:
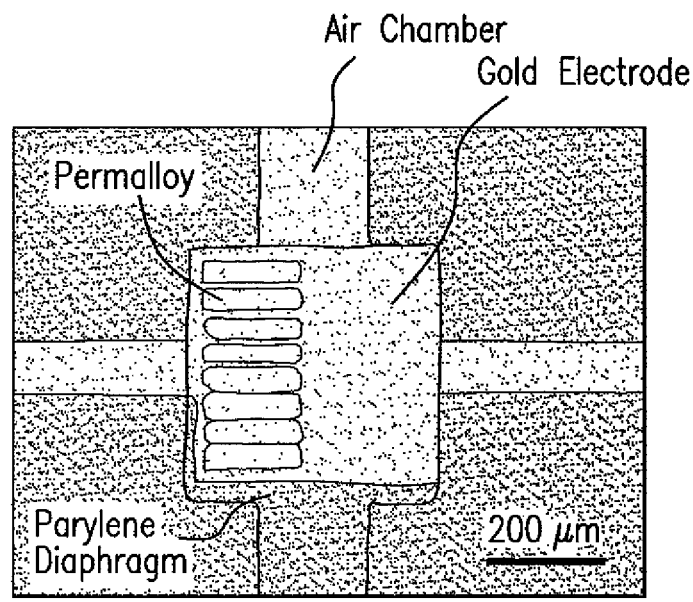
FIGS. 12A-B are images of a MEMS affinity glucose sensor (A) before and (B) after packaging and putting into the measurement system.
Figure 12B:
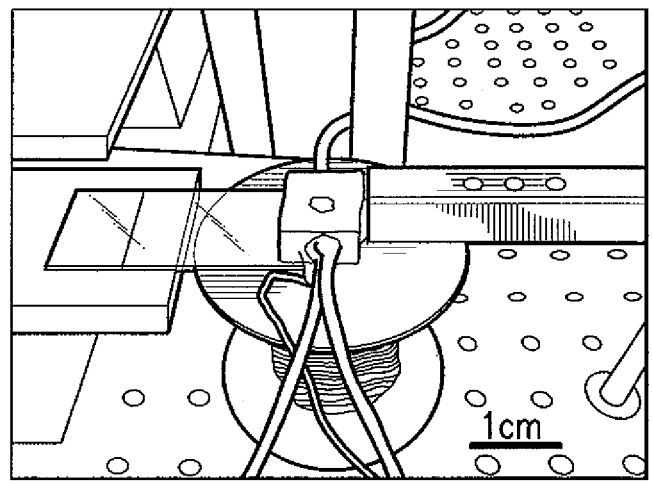
Figure 21A:
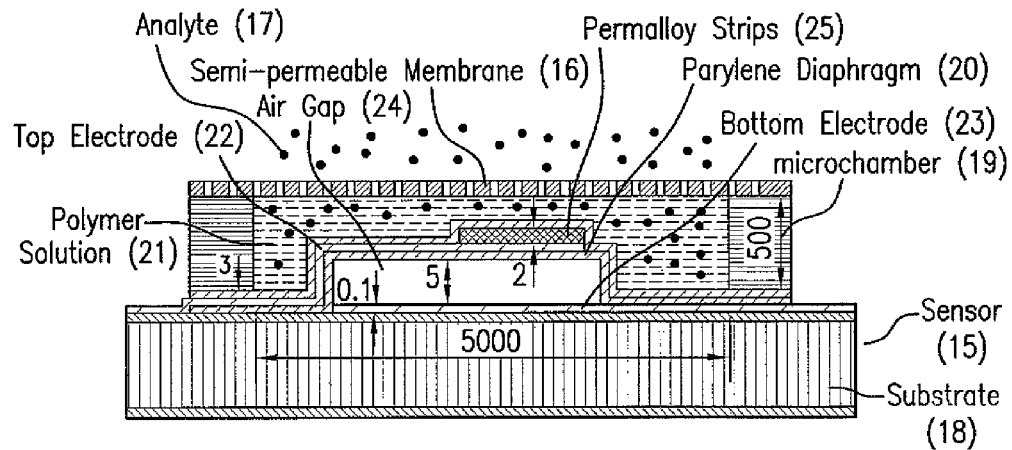
FIGS. 21A-B are schematics of the MEMS capacitive glucose sensor: (A) side-view of the capacitive glucose sensor; (B) top-view of the capacitive glucose sensor (Dimensions are given in µm).
Figure 21B:
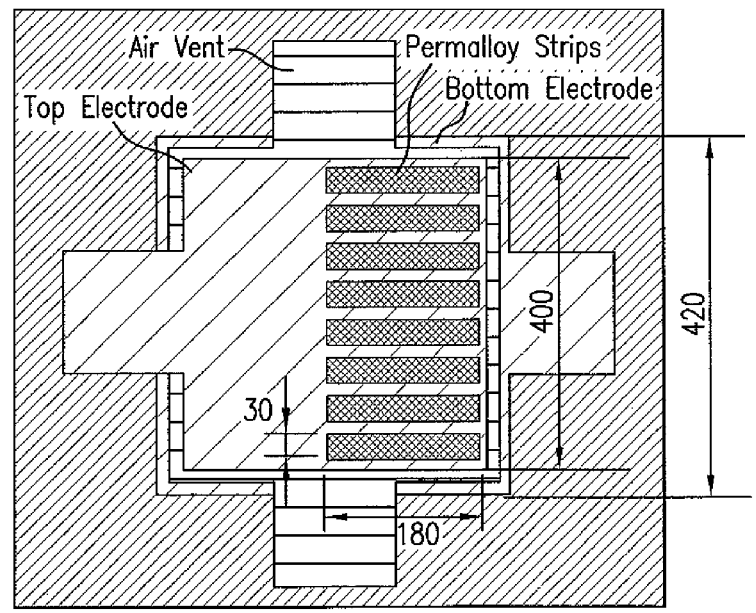
Figure 22A:
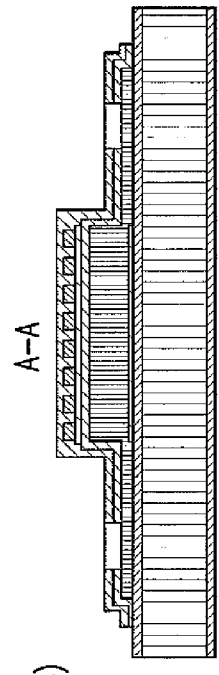
FIGS. 22A-F are a diagram illustrating an exemplary fabrication process: (A) bottom gold electrode deposition and sacrificial layer patterning; (B) Parylene deposition and top gold electrode deposition; (C) permalloy electroplating and additional Parylene layer deposition; (D) photoresist etching holes patterning; (e) sacrificial layer removal and diaphragm releasing; (f) membrane bonding and sensor packaging.
Figure 22B:
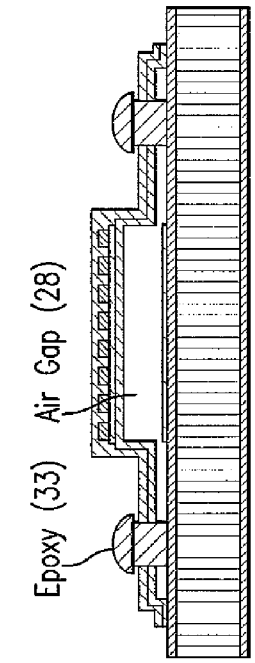
Figure 22C:
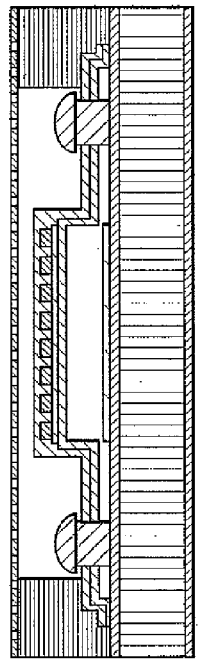
Figure 22D:
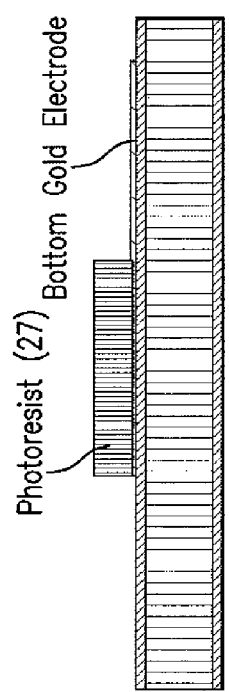
Figure 22E:
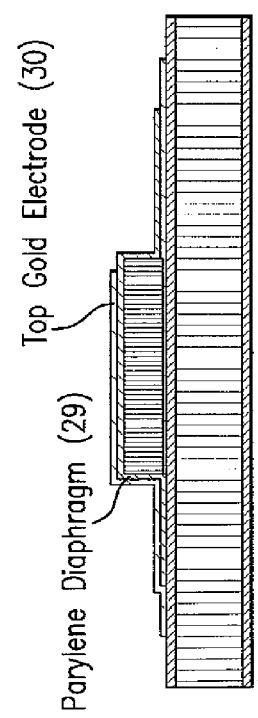
Figure 22F:
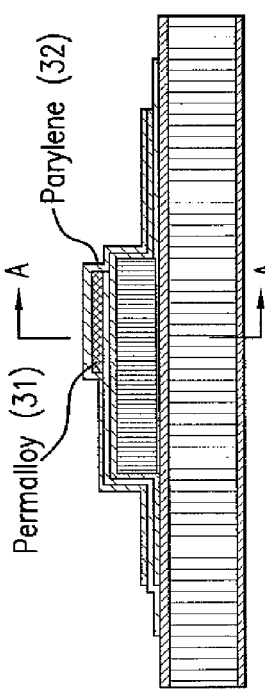

In a different embodiment of the disclosed subject matter, the sensor is a viscosity-based sensor that includes a vibrational diaphragm, which is also referred as "diaphragm-based sensor." In these embodiments, the diaphragm can be made of any applicable polymer known in the art, including but not limited to the polymer Parylene. In specific embodiments, the diaphragm can be a Paralene membrane. The vibrational Parylene diaphragm can be situated inside a microchamber, as shown in FIGS. 12A and 21. The microchamber is filled with the solution of a biocompatible polymer that binds with the analyte, and is equipped with a cellulose acetate semi-permeable membrane, which allows the analyte to permeate into and out of the chamber while keeping the polymer from escaping. In one embodiment, the diaphragm is embedded with a moving top electrode, which forms a capacitor with a fixed bottom electrode. Separating the electrodes is a sealed air gap. A set of permalloy thin-film strips are also integrated on the diaphragm. The permalloy and moving top electrode are passivated by additional Parylene layer to avoid direct contact with the polymer solution. The interaction of the polymer and the analyte leads to increased vibrational damping of the Parylene diaphragm, thus producing a measureable capacitance change across the metal electrodes. The capacitance changes are defined as the difference between the sensor capacitance values with and without the presence of the analyte.

When the analyte permeates through the semi-permeable membrane, it interacts with the polymer to result in a viscosity change, which is detected via vibration measurements. Specifically, an externally applied time varying magnetic field acts upon the permalloy strips, which are magnetized along their length by a permanent magnet. This results in a time varying moment in the permalloy, directed in the in-plane direction perpendicular to the strip length. Under the action of the moment, the diaphragm vibrates, whose deflection is detected from the capacitance change between the electrodes. As the viscous damping on the vibration directly depends on the viscosity, the measured capacitance change can be used to determine the viscosity change, and hence the presence and property of the analyte, for example, the concentration of the analyte.

In one embodiment, as shown in FIG. 21, a sensor 15 includes a semi-permeable membrane 16 which is permeable to a sample analyte 17, a substrate 18, and a microchamber 19 which includes a Parylene diaphragm 20. The microchamber 19 is filled with a solution of polymer 21 that binds with the analyte 17. The semi-permeable membrane 16 allows the analyte 17 to permeate into and out of the microchamber 19 while keeping the polymer 21 from escaping. The Parylene diaphragm 20 is embedded with a moving top electrode 22 within the microchamber 19, which forms a capacitor with a fixed bottom electrode 23. The bottom electrode 23 is separated from the Parylene diaphragm 20 and top electrode 22 by a sealed air gap 24. A set of permalloy thin-film stripes 25 are integrated on the Parylene diaphragm 20. The permalloy film stripes 25 and top electrode 22 are passivated to avoid direct contact with the solution of polymer 21. The polymer includes, but is not limited to a polymer having a plurality of boronic acid moieties, for example, PAA-ran-PAAPBA.

The diaphragm vibration is in general a complex physical phenomenon involving the intimate coupling of the motion of the continuously deflecting diaphragm and the flow of the viscous polymer solution. Nonetheless, useful insight can be gained into this phenomenon with a simplified analysis, in which the diaphragm was represented as a one-degree-of-freedom (1-DOF) mass-spring-damper system. In one embodiment, the permalloy strips are collectively represented as a 1-DOF rigid plate that can rotate about a fixed axis under a magnetically applied torque. The diaphragm outside the plate region is assumed to have negligible inertia while applying a linear elastic restoring torque on the plate. The interaction of the plate and diaphragm motion with the polymer solution can be represented as a linear viscous torque. Then the equation governing the plate rotation, $\theta$, under a torque, $T(t)$, takes the form:

$$I\ddot{\theta}+D\dot{\theta}+K\theta=T(t) \quad (2)$$

where I is the plate's moment of inertia, D the viscous damping coefficient, and K the diaphragm's spring constant.

Consider the steady-state motion of the permalloy plate under a harmonic magnetic excitation, $T(t)=T_m e^{i\omega t}$, at frequency $f=\omega/2\pi$. Equation (2) can be reformulated into a form:

$$\ddot{\theta}+2\zeta\omega_0\dot{\theta}+\omega_0^2\theta=\theta_m e^{i\omega t} \quad (3)$$

where $\omega_0=2\pi f_0=(K/I)^{1/2}$ is the natural frequency, and $\xi=\frac{1}{2}D/(IK)^{1/2}$ is the dimensionless damping ratio. In addition, $\theta_m=T_m/K$ is the plate rotation at zero excitation frequency.

The steady-state solution to Equation (3) is of the form $\theta=Ae^{-i\phi}e^{i\omega t}$, where $Ae^{-i\phi}$ is the complex amplitude with the amplitude (A) and phase shift ($\phi$) of the plate rotation respectively. By defining $p=f/f_0$, these quantities are given by $$A_x=A\cos\phi=\theta_m(1-p^2)/[(1-p^2)^2+4\zeta^2 p^2] \quad (4)$$

$$A_y=A\sin\phi=\theta_m(2\zeta p)/[(1-p^2)^2+4\zeta^2 p^2] \quad (5)$$

Figure 27:
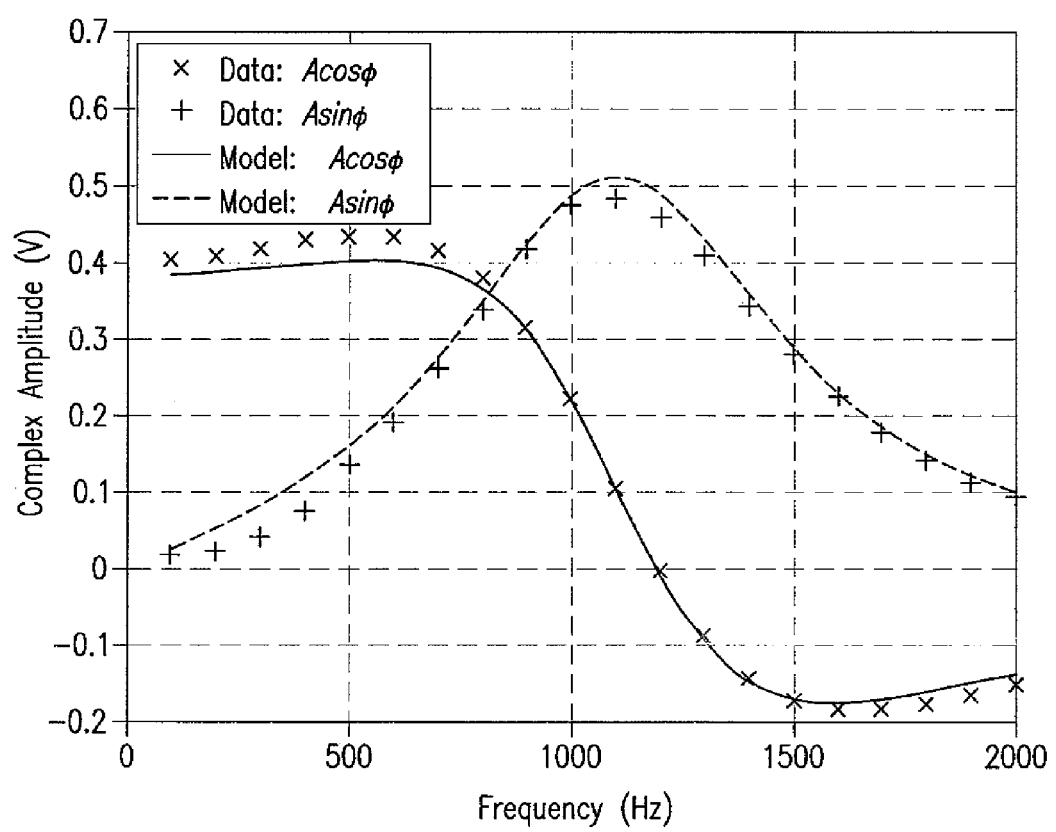
FIG. 27 is a chart illustrating 1-DOF mass-spring-damper model fitted to the experimental data obtained at a glucose concentration of 90 mg/dL.
Figure 28:
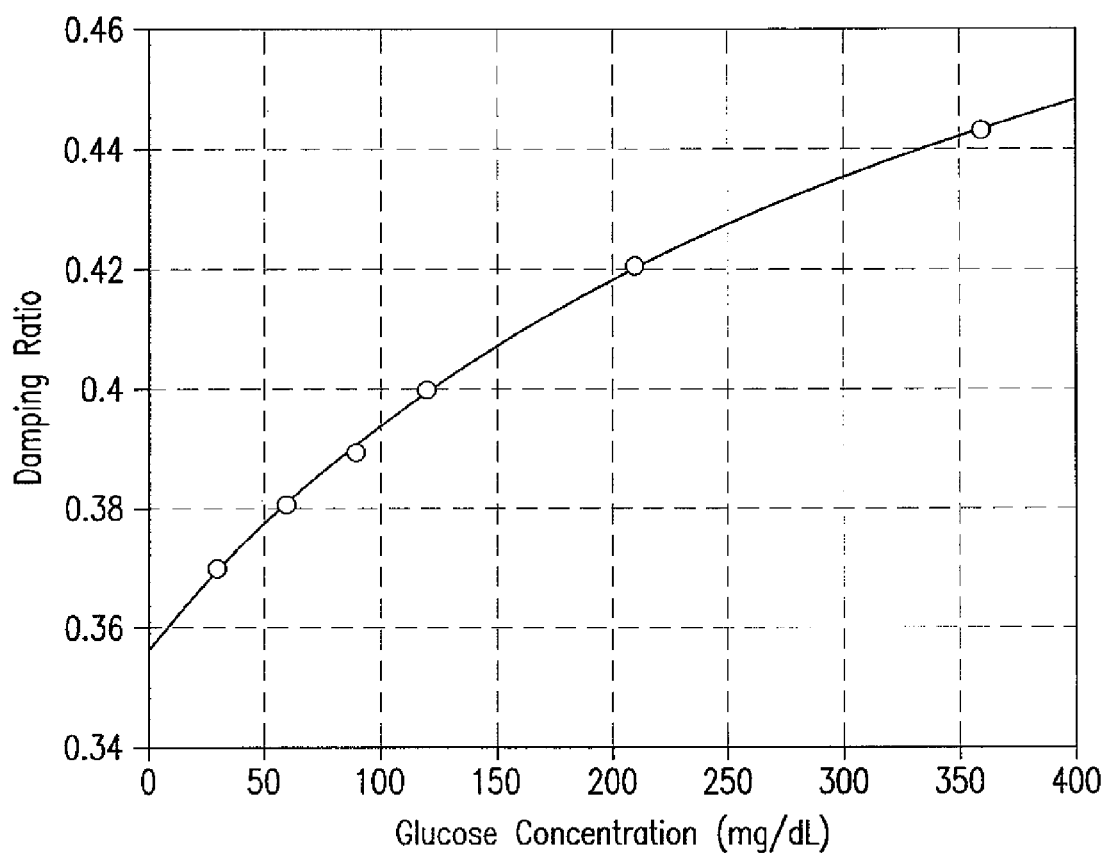
FIG. 28 is a chart illustrating damping ratio obtained by fitting the 1-DOF mass-spring-damper model to the experimental data at varying glucose concentrations.

Equations (4) and (5) can be fitted to the experimental data, recognizing that the diaphragm rotation is proportional to the sensor output. For example, when the analyte of interest is glucose, a 1-DOF mass-spring-damper model fitted to the experimental data obtained at a glucose concentration at 90 mg/dL is shown in FIG. 27. It is important to note that to obtain consistent results, it is not appropriate to fit $A_x$ or $A_y$ (or equivalently A or $\phi$) independently to the data. Instead, it is necessary to fit a vector-valued function $\{A_x, A_y\}$ as a function of f as given in Equations (4) and (5) to the experimental data, yielding consistent estimates of the parameters $\theta_m$, $f_0$, and $\xi$. As shown in FIG. 27, a least-square fit yields the following estimates: $f_0=1190$ Hz and $\theta_m=0.38$ V, with $\xi=0.39$, which shows the model agrees with the experimental data well, considering that the fitting involves a vector-valued function, i.e., the model must fit two sets of experimental data with a single set of parameter estimates. The model given by Equations (4) and (5) can also be fitted to experimental data obtained at other glucose concentrations as shown in FIG. 27. The value of $\theta_m$ is consistently estimated to be almost constant at 0.38 V, with variations less than 0.9% as the glucose concentration varies from 30 to 360 mg/dL. In addition, the estimated natural frequency $f_m$ changes only by 0.6%, suggesting that inertial contributions of viscous effects are insignificant. As shown in FIG. 28, the damping ratio estimated from the fits increases steadily, by 20% as the glucose concentration varies from 30 to 360 mg/dL. This is consistent with increased viscosity of the polymer solution at elevated glucose concentrations.

FIG. 22 illustrates an exemplary manufacturing process for the diaphragm-based sensor. The fabrication process begins with the deposition and patterning of chrome (5 nm) and gold (100 nm) to form the fixed bottom electrode 26 on the thermally grown $SiO_2$ layer on a silicon wafer (420×420×0.1 µm). A sacrificial photoresist layer 27 (5 µm) is then spin-coated and patterned to define an electrode air gap 28 (see FIG. 22A), followed by the deposition of a Parylene Diaphragm 29 (3 µm). A second layer of chrome (5 µm) and gold (100 nm) are next deposited for the moving top electrode 30 and permalloy seed layer (see FIG. 22B), Subsequently, with the permalloy strips defined by a photoresist mold (5 µm), permalloy 31 (2 µm) is electroplated. This is followed by the removal of the photoresist mold, patterning of the moving top electrode 30, and deposition of an additional Parylene layer 32 (3 µm) for passivation (see FIG. 22C). Two etching holes (500×500 µm) are opened through the two Parylene layers 29 and 32 by oxygen plasma to expose the sacrificial photoresist layer (see FIG. 22D), which is subsequently removed by acetone (80° C.) to release the diaphragm 29. These two etching holes are then sealed by epoxy 33 (Devcon) (see FIG. 22E). After wafer dicing and wire bonding, a chip is bonded to a polycarbonate sheet (thickness: 500 µm), in which holes of appropriate sizes are drilled to define the microchamber as well as the inlet and outlet (each 10 µL) for polymer solution handling. The polycarbonate is in turn bonded to a semi-permeable membrane (regenerated cellulose acetate with a molecular weight cutoff of 3500; Fisher Scientific) using epoxy (see FIG. 22F).

Permittivity-Based Sensor

In another embodiment of the disclosed subject matter, the sensor for monitoring a target analyte is a "permittivity-based sensor", which adopts permittivity measurements. The permittivity-based sensor employs a solution of a biocompatible polymer, for example, PAA-ran-PAAPBA which contains phenylboronic acid moieties that specifically bind to the analyte. A chamber between two parallel-plate electrodes, a top electrode and a bottom electrode, is filled with a solution of the polymer. The electrodes are imposed with an AC electric field which causes the polarization of the polymer manifested as a permittivity. The binding between the polymer and the analyte causes the polymer to crosslink, thereby changing the polarization behavior and hence permittivity of the polymer. Thus, measuring the capacitance between the electrodes allows monitoring the presence and property of the analyte, including, but not limited to, determining the concentration of the analyte. In one embodiment, the permittivity-based sensor consists of a pair of parallel-assembled glass coverslips each coated with a thin-film copper electrode. The gap between the electrodes, defined by a photoresist spacer layer, is filled with PAA-ran-PAAPBA solution mixed with glucose, as shown in FIG. 15A.

Figure 15B:
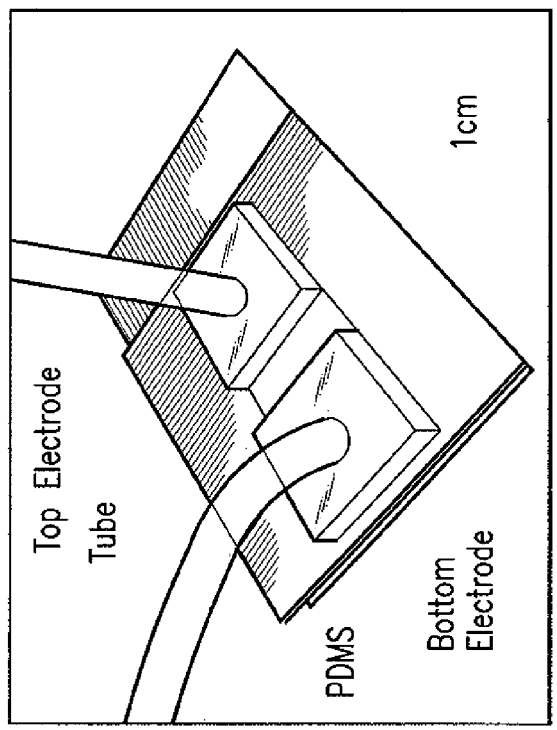
FIGS. 15A-B are diagrams illustrating an exemplary glucose sensor design in accordance with the disclosed subject matter and an image of a fabricated sensor.
Figure 15A:
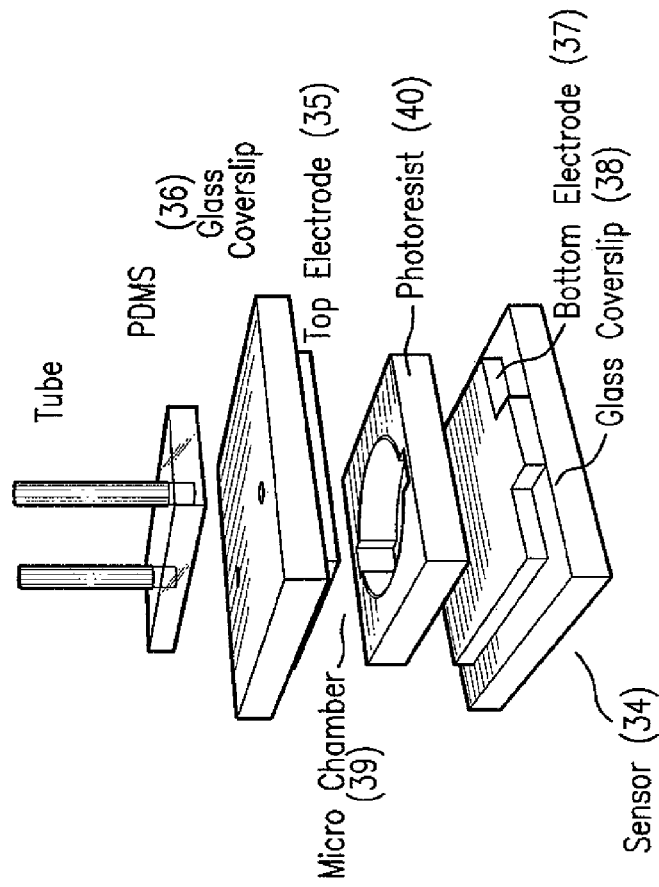

One embodiment of a permittivity based sensor is shown in FIG. 15A, a sensor 34 has a top electrode 35 which is embedded with a glass coverslip 36, a bottom electrode 37 which is embedded with a glass coverslip 38, and a chamber 39 between the top electrode 35 and the bottom electrode 37 defined by a photoresist layer 40. The chamber 39 is filled with a solution of polymer. The polymer includes, but is not limited to a polymer having a plurality of boronic acid moieties, for example, PAA-ran-PAAPBA.

Another embodiment of a permittivity based sensor is shown in FIGS. 32A-C. The device consisted of a microchamber 50, filled with an aqueous solution. Two gold electrodes deposited on the top 51 and bottom 52 chamber walls were patterned to the chamber shape and dimensions. A gold thin-film temperature sensor 53 was also integrated on the bottom chamber wall. An AC E-field imposed on the electrodes caused the polarization of the polymer polarization, which directly depended on glucose binding. Thus, the permittivity could be obtained to determine the glucose concentration.

Under an electric field (E-field), a dielectric material dissolved or suspended in a liquid phase undergoes a charge separation and molecular redistribution, resulting in electric polarization, i.e., a regular rearrangement of charged particles such as electrons, ions, and molecules. If the E-field is periodically varying in time, the polarization can be frequency dependent as the particle rearrangement does not respond instantaneously to the field variations. The frequency-dependent polarization is represented by the complex permittivity, whose real part is related to the stored electric energy within the material, and whose imaginary part represents the dissipation or loss of energy within the material. The permittivity, as a macroscopic property, is related to the molecular structure of the material through the polarizability and the molecular dipole moments. In the context of affinity biosensors, the dielectric material contains a receptor group for a molecular target. When the receptor binds to the target molecules, the material can undergo a structural change as well as alteration of the overall dipole moments. This can be manifested in terms of changes in the permittivity, which can be used to determine the concentration of the bound molecules.

An exemplary manufacturing process for the permittivity-based sensor, for example, a sensor as shown in FIG. 15A, begins with the deposition and patterning of copper electrodes on two glass slides. Photoresist, for example, AZ P4620, is then spin-coated on these two glass slides to prevent the direct contact between the polymer solution and the electrodes. Another photoresist layer is then coated and patterned on one of the glass slide to create a chamber for introduction of the polymer solution. Finally, these two glass slides are aligned and glued together by photoresist reflowing.

In another embodiment, the manufacturing process of the device shown in FIG. 32A includes a gold thin film 100 nm thick deposited by thermal evaporation and patterned to form the electrodes on the top and bottom glass slides, as well as the temperature sensor 53 on the bottom slide. Passivation photoresist layers can be spin-coated on the glass slides to prevent the direct contact of the electrodes with the dielectric solution. Another photoresist layer can then be deposited and patterned on the bottom glass slide to define the microchamber along with an inlet and an outlet for introduction and removal of the polymer solution. The top glass slide is next placed over the bottom slide and aligned to form the microchamber along with a parallel-plate capacitor comprised of the two electrodes. The photoresist layers can be baked at a set temperature for a set number of minutes on a hotplate, causing the reflow of the photoresist and bonding of the glass slides to complete the device fabrication. Images of a fabricated device before and after packaging are shown in FIGS. 32B and C.

Polymer Solution

The sensor as provided in the presently disclosed subject matter can have many applications and therefore can be used to monitor a number of target analytes. In selecting a target analyte, an appropriate polymer solution must be used in the sensor.

In one embodiment, the biocompatible polymer can reversibly and specifically binds to the analyte of interest. The binding between the polymer and the analyte can result in changes of the physical characteristics (e.g., the viscosity and/or permittivity) of the polymer, which can be measured to extrapolate the presence and amount of the analyte in the sample. The polymer specially responds to the analyte of interest. For example, in one embodiment, the analyte is glucose, through proper adjustment of the composition percentage of the boronic acid moieties on the polymer and polymer concentrations, the polymer can detect and differentiate glucose from other monosaccharides and disaccharides. Thus, the polymer can be highly specific response to glucose. Applying this polymer to the sensor as disclosed herein will enable highly reliable, continuous monitoring of glucose in ISF in subcutaneous tissue.

In one embodiment, the binding between the polymer and the analyte of interest is reversible. In another embodiment, the ester bonds formed between the polymer and glucose can be broken to substantially recover the polymer and/or the sample containing glucose. For example, dialysis of the glucose cross-linked polymer using water and passing through a semi-permeable membrane can result in significant decreases of viscosity. This decrease in viscosity is due to the loss of the ester bonds between the boronic acid moieties of the polymeric backbone and the glucose in the sample. As such, the polymer can be recovered and reused to test other samples for the presence of glucose.

In one embodiment, a suitable polymer having boronic acid moieties can be formed as a copolymer of at least two monomers, where one of the monomers includes at least one boronic acid functional group. A copolymer can be synthesized with these monomers via classic free radical copolymerization processes. In one embodiment, a copolymer is PAA-ran-PAAPBA. In various embodiments, a suitable polymer includes, but is not limited to, a polymer that contains boronic acid groups, or other receptor groups that recognize the given analytes.

Figure 31A:
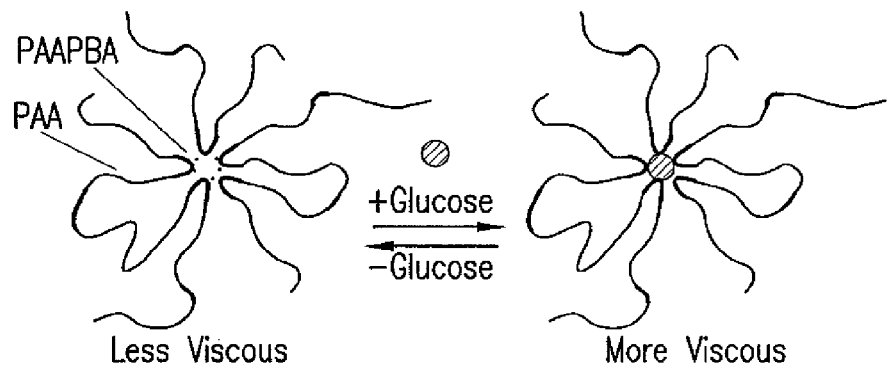
FIGS. 31A-B are diagrams illustrating a biocompatible, glucose-sensitive polymer, PAA-ran-PAAPBA. (A) The polymer composition and mechanism of interaction with glucose. (B) Glucose-induced viscosity change of a 1.9% PAA-ran-PAAPBA solution in PBS buffer (pH 7.4). (C) Glucose-induced viscosity change of a 5% PAA-ran-PAAPBA solution in PBS buffer (pH 7.4).

PAA-ran-PAAPBA is an amphiphilic copolymer containing two components, hydrophilic polymer segment polyacrylamide (PAA) and hydrophobic polymer segment poly(3-acrylamidophenylboronic acid) (PAAPBA) (see FIG. 31A). PAAPBA is the glucose-sensitive component, containing boronic acid groups which can form cyclic boronate esters in aqueous media after binding with glucose. PAA, which is water soluble, serves to improve the water solubility of the hydrophobic PAAPBA segment. In addition to being a water soluble component, PAA provides an added neighbor coordinating effect by carbonyl oxygen and boron chelating which enhances the binding between the boronic acid and carbohydrates (Li S. et al., J. Diabetes Sci. Tech. (2008); 2(6):1066-1074). The polymer is synthesized by a free radical polymerization process, e.g., as is described in detail in Li S. et al. (2009); Li S. et al. (2008) (Li S. et al., Biomacromolecules (2009); 10:113-118; Li S. et al., (2008)).

Figure 31B:
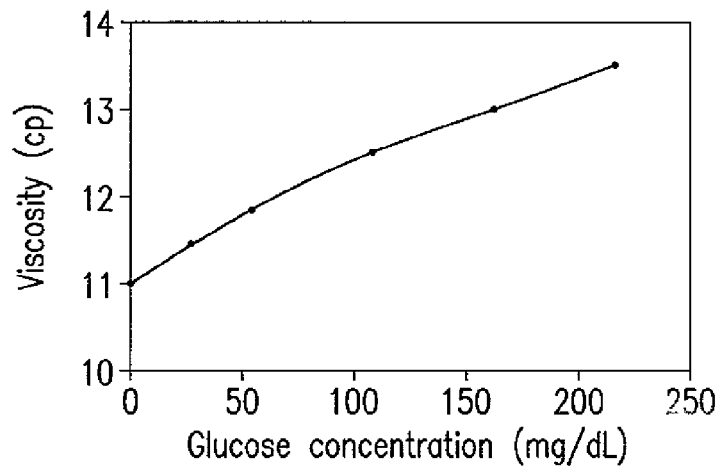
Figure 31C:
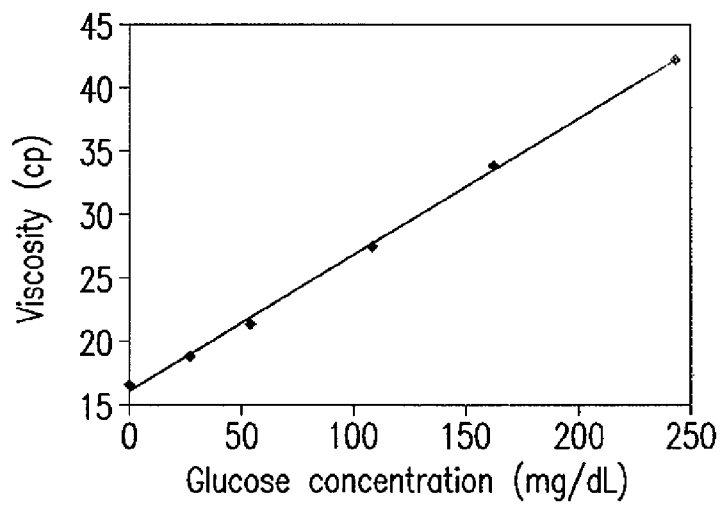

A solution of PAA-ran-PAAPBA undergoes a viscosity change when interacting with glucose molecules. That is, when glucose is added to the PAA-ran-PAAPBA solution, the phenylboronic acid moieties in the polymer are able to reversibly form strong ester bonds with the glucose at a ratio of two to one on the PAA-ran-PAAPBA polymer backbone, resulting in the cross-linking of the polymer and hence a conformation change. This leads to a shorter distance between polymer chains and a further aggregation of the polymer, thus resulting in an increase in the viscosity of the polymer (see FIG. 31B-C), which can be detected by the sensor provided in the disclosed subject matter. The viscosity change is reversible due to the reversibility of the polymer-glucose binding, and is highly specific to glucose over other saccharides as experimentally verified elsewhere (Li S. et al., (2009); Li S. et al., (2008)).

In addition, a solution of PAA-ran-PAAPBA polymer undergoes dielectric property changes when interacting with glucose molecules. AAPBA segments bind with glucose at a two to one ratio, leading to the reversible formation of cyclic esters of boronic acid. That is, the binding of a glucose molecule results in the elimination of two hydroxyl groups. Thus, given an equilibrium dissociation constant on the order of 1.6 mM for the affinity binding system, it can be estimated that up to about 11% of permanent dipoles are lost over the glucose concentrations tested. This directly reduces dipole reorientation effects. In addition, due to an overall charge decrease on polymer segments as well as changes in polymer conformations that alter the electric double layer structure, the glucose binding reduces Maxwell-Wagner-Sillars and counterion polarization effects. These lead to a decrease in the permittivity of the polymer, which can be detected by the sensor provided in the disclosed subject matter.

Applications of the Sensor

In various embodiments of the disclosed subject matter, the sensor can be used to determine the level of an analyte in the body, for example oxygen, lactase, insulin, hormones, cholesterol, medicaments, viruses, or the like. The sensor can use any known method to provide an output signal indicative of the concentration of the target analyte. The output signal is typically a raw data stream that is used to provide a useful value of the measured analyte concentration to a patient or doctor, for example.

In a specific embodiment of the disclosed subject matter, the sensor is used to monitor glucose as the target analyte. In these embodiments, the sensor can measure a concentration of glucose or a substance indicative of the concentration or presence of the glucose by using a specific polymer in the sensor. In one embodiment, the polymer has boronic acid functional groups extending from the polymeric backbone (i.e., the boronic acid moieties) that allows glucose to reversibly form ester bonds with the boronic acid moiety. These bonds can result in cross-linking of the polymers in the system, which leads to an increase in the solution viscosity. The viscosity of the polymer can become steady within minutes upon changing glucose concentrations. The polymeric composition can be configured such that a viscosity increase can be observed when glucose concentration increases. For example, a viscosity increase can be observed when glucose concentration increases from about 0 to about 25 mM. In another embodiment, the cross-linking of the polymers resulted from the binding between the polymer and glucose leads to a change in the polarization behavior of the polymer, and hence changes the permittivity of the polymer.

The sensor can also be used for other applications. In addition to diabetes, the proposed miniature CGM device can also be used for glucose monitoring for other diseases (e.g., glycogen storage disease and hyperinsulinaemic hypoglycaemia).

The method can be extended to other metabolites, such as lactate, fatty acids, cysteines and homocysteines. For example, in emergency medicine, lactate monitoring can be used to predict possible organ failure of trauma patients, organ transplant patients, and patients with other critical conditions.

Further, the methods disclosed herein can be used as a reliable method for long-term monitoring of metabolites. Such methods can have great military significance. For example, a miniature device for glucose detection with fully electronic readout would have significant applications in protecting armed forces in the field. It would also provide a platform to enable the delivery of drug treatments and nutritional supplements to protect and enhance performance in military personnel.

Moreover, the disclosed method can be applied to the diagnosis of disease. For example, the development of boronic acid based glucose sensing systems can be potentially extended to other analytes, such as human viruses and bacteria, since most of those microorganisms carry glycoproteins on the exterior surface that can be targeted by the boronic acid based binding motifs.

Finally, metabolic monitoring is of great utility to environmental monitoring. Changes in the concentrations of metabolites are the precursors and products of enzymatic activity, and can be associated with biological function and regulation. Metabolic monitoring hence can be used for environmental monitoring, e.g., risk assessment of chemicals and diagnosis of diseases in wild animals. It can also be used as a tool to better understand the underlying mechanisms of action of toxic compounds in the environment.

EXAMPLES

The disclosed subject matter will be better understood with reference to the following Example, which is provided as exemplary of the disclosed subject matter, and not by way of limitation.

Example 1

A MEMS Affinity Glucose Sensor Using a Biocompatible Glucose-Responsive Polymer In the present example, a sensor having a vibrational cantilever is used and tested for monitoring the concentration of glucose.

Experimental Method

Figure 9:
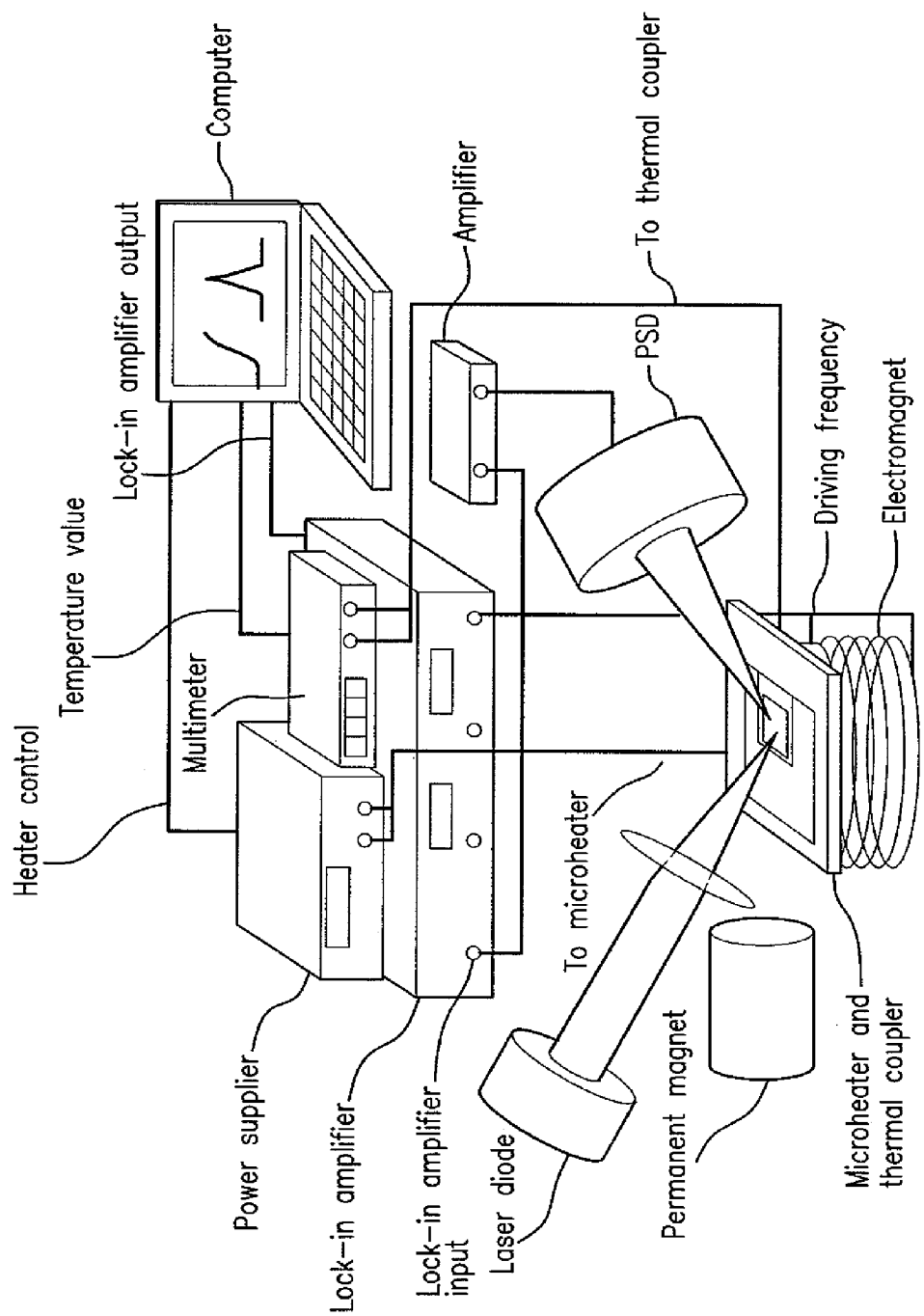
FIG. 9 is a diagram illustrating an experimental setup for characterization of a MEMS glucose sensor in accordance with the disclosed subject matter.

The sensor consists of a Parylene cantilever which vibrates under magnetic excitation inside a microchamber. The microchamber is filled with a solution of PAA-ran-PAAPBA that specifically recognizes glucose by affinity binding. The microchamber is sealed with a cellulose acetate semi-permeable membrane, which prevents the polymer from escaping while allowing permeation of glucose into and out of the chamber (FIG. 1). Affinity binding between the polymer and glucose results in the cross-linking of the polymer and an increase in the viscosity of the polymer solution. Thus, by measuring the damped cantilever vibration in the solution, the glucose concentration can be determined. The fabrication process and experimental setup of the sensor are shown in FIGS. 2 and 9, respectively. The cantilever vibration was measured with an optical lever system as shown in FIG. 9.

Chemical reagents used in the experiments include d-(+)-glucose (Sigma-Aldrich) and PAA-ran-PAAPBA that is synthesized using a method described in Li S. et al., (2009). Phosphate buffer saline (PBS), pH 7.4, was prepared from potassium phosphate (20 mM), NaCl (150 mM) and $NaN_3$ (0.05%). Glucose stock solution (1 M) was prepared by dissolving glucose (1.8 g) in PBS to 10 mL. A series of glucose solutions (27 mg/dL, 54 mg/dL, 108 mg/dL, 216 mg/dL, and 324 mg/dL) were prepared by further diluting the stock solution with PBS. To prepare polymer solutions that were mixed with glucose before being loaded into the microchamber, PAA-ran-PAAPBA solution (1 mL, 0.45 mg/dL) and glucose (6 μL, 1 M) were mixed to obtain 108 mg/dL glucose concentration in PAA-ran-PAAPBA solution. PAA-ran-PAAPBA copolymer solution with 1.9%, 2.3%, 4.3%, 5%, and 7.3% of PAAPBA composition was prepared using a method described in Li S. et al. (2008)). PAA-ran-PAAPBA (284 mg, with 1.9% of PAAPBA in the polymer) was dissolved in PBS (6 mL) to obtain the sensing solution.

All experiments were conducted at 37° C. with closed-loop temperature control by placing the sensor on an ultra-thin kapton heater with temperature measured by a k-type thermocouple. This was necessary so as to minimize temperature-dependent viscosity changes in the fluids, and provide a physiologically relevant glucose monitoring condition. The thermocouple was connected to a multimeter (Agilent 34420A Nano Volt/Micro Ohm meter) to obtain temperature measurements. These values were then transmitted to a computer to control the voltage output of the DC power supply (Agilent E3631A DC power supply) connected to the heater. In all experiments unless otherwise noted, the sensor's microchamber was filled with a glucose-free polymer solution (1.9%), while glucose solutions of varying concentrations were introduced into the test cell. Glucose permeated through the semi-permeable membrane and bound to the polymer, until this process reached equilibrium. Because the volume of the test cell was 20 times than that of the chamber, it was reasonable to assume that the equilibrium glucose concentration equaled the initial glucose concentration in the test cell.

The cantilever vibration was driven by a hand-wound solenoid (4000 turns of a 200 μm diameter copper wire on a 2.5 cm diameter plastic core), which under a 5 $V_{rms}$ driving voltage generated an electromagnetic of approximately 0.8 kA/m perpendicular to the cantilever surface. A permanent magnet with field strength of 500 kA/m was placed parallel to the cantilever surface to magnetize the permalloy film. The cantilever vibration was detected by an optical-lever system as described in Zhao Y. et al. (Zhao Y. et al., (2007)). Briefly, a laser beam was directed onto and reflected off of the free end of the cantilever. Detection of the reflected laser beam using a position sensitive detector allowed determination of the cantilever deflection.

Results and Discussion

1. Binding Ability of Copolymer

Figure 13:
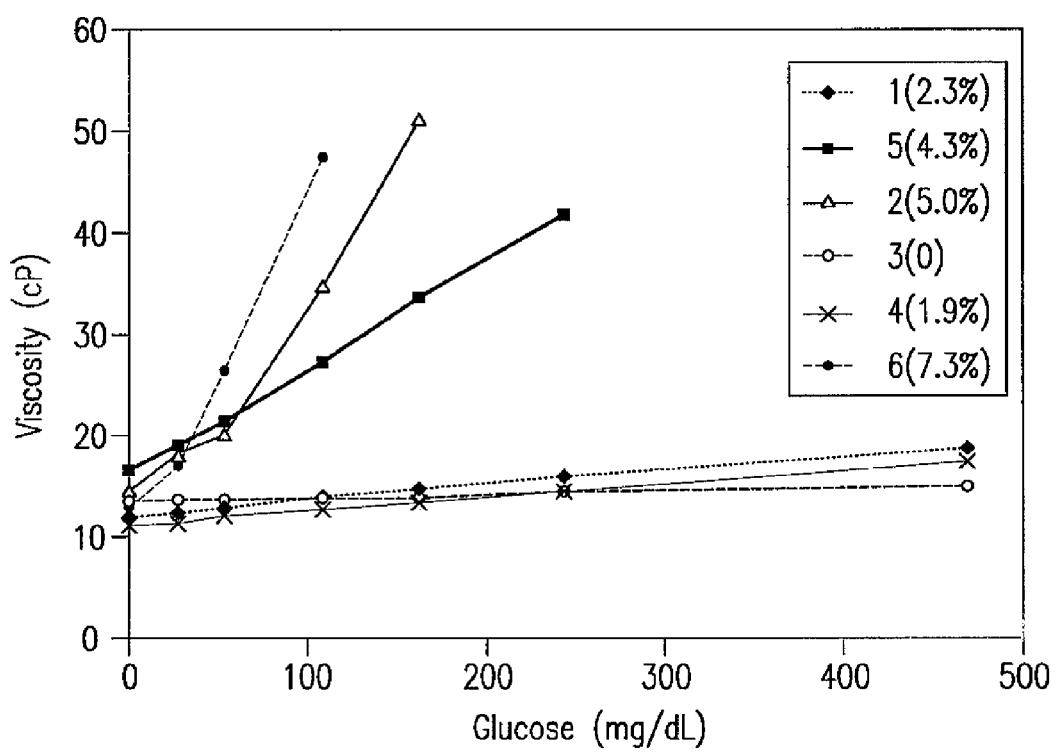
FIG. 13 is a chart illustrating viscosity responses of polymers of different molecular weight and PAA-ran-PBA percentage.

To investigate the binding ability of the copolymer with the glucose molecules, a series of copolymer solutions with varying PAAPBA composition (1.9% to 7.3%) were synthesized. An Ubbelohde viscometer (CANNON® Instrument Company) was used to measure the viscosity change in the copolymer solution after its interaction with glucose molecules. As shown in FIG. 13, polymer 1 and 4 with about 2% PAAPBA had similar responses to glucose concentration from 0 to 918 mg/dL, while polymer 1 showed a higher viscosity due to an increased PAAPBA percentage. Comparably, copolymer solutions with a PAAPBA moiety larger than 4.3% exhibited a dramatic change in viscosity with increasing glucose concentration, indicating significantly enhanced sensitivity to viscosity with higher PAAPBA content. The control polymer 3 (using N-phenylacrylamide (NPAA) instead of N-3-acrylamidophenylboronic acid (AAPBA) as the monomer) had no boronic acid group in the polymer. It was highly inert to the glucose concentration change, indicating that AAPBA was indeed the glucose-reactive component in the copolymer. Since a higher PAAPBA percentage would significantly increase the viscosity of the polymer solution and the damping to the cantilever vibration, a 1.9% PAAPBA copolymer solution was more preferable in the following MEMS sensor experiments to minimize the damping of the cantilever vibration and ensure large cantilever response.

Figure 14:
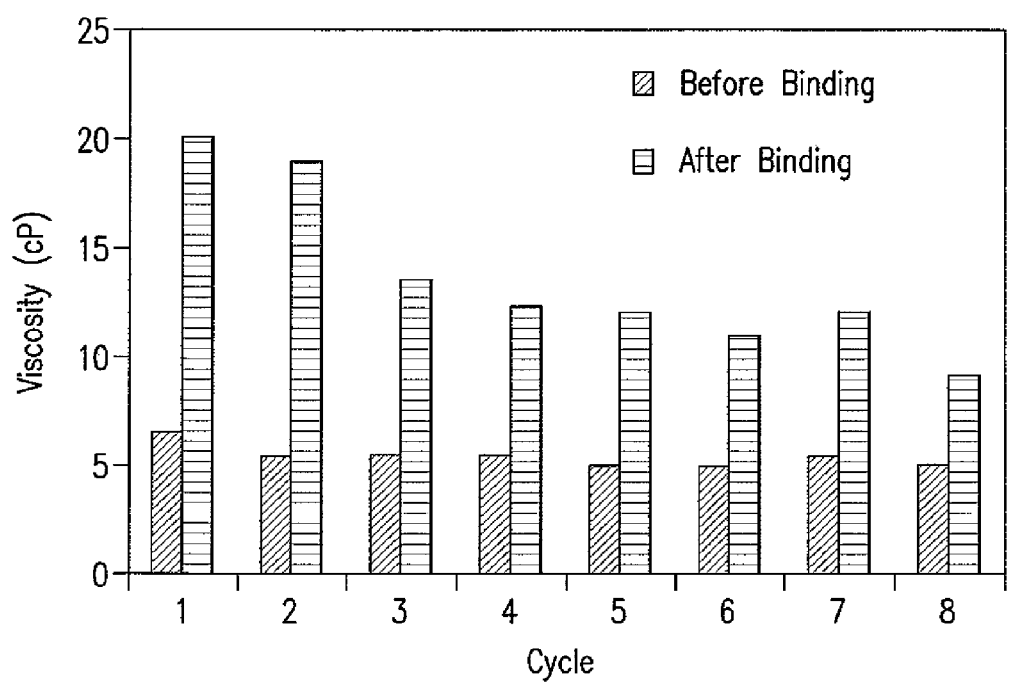
FIG. 14 is a chart illustrating reversibility of the copolymer (4.7%) to glucose concentration changes.

The reversibility of the PAA-ran-PAAPBA copolymer, indicating the stability of this copolymer over time, was measured using the Ubbelohde viscometer. A 4.7% copolymer solution retained inside a semi-permeable dialysis tubing, was repeatedly immersed into a PBS buffer and 450 mg/dL glucose solution. The blank copolymer solution showed a viscosity of 6.4 cP. In the glucose solution, the viscosity increased to 20.4 cP. After dialysis against PBS buffer, its viscosity significantly dropped to 5.4 cP (FIG. 14), indicating that removal of glucose dissociated the crosslinking network and lowered the viscosity of the copolymer solution. The viscosity after copolymer/glucose binding was slightly different over time, which can be attributed to the loss of polymer on the dialysis sensor.

2. Response Time

Figure 4:
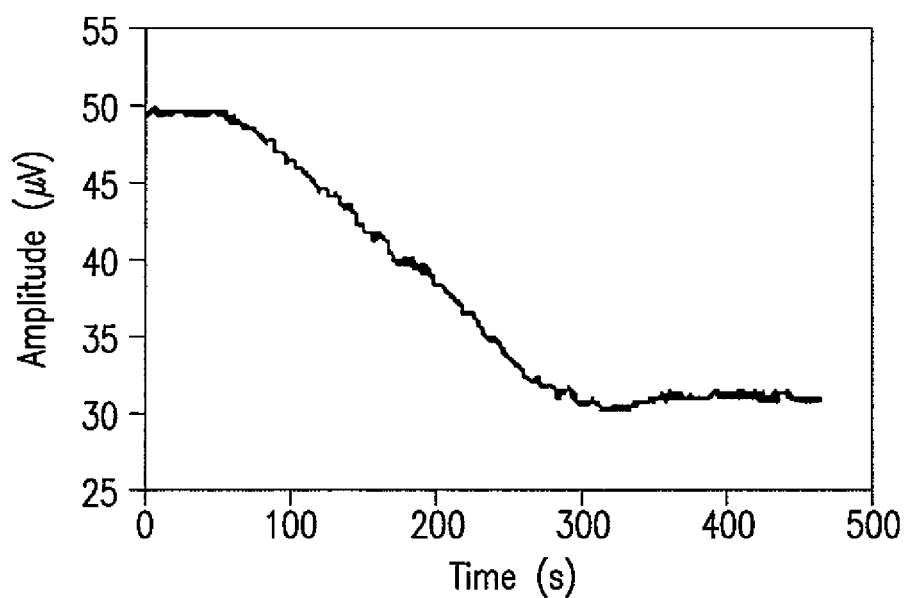
FIG. 4 is a chart illustrating variation with time of the cantilever vibration amplitude at 28 Hz upon introduction of a 108 mg/dL glucose solution to the sensor. Glucose was initially absent from the solution of polymer in the microchamber.

To characterize the response time of the sensor to glucose concentration change, the time constant of an experiment involving glucose permeation through the membrane and binding to the polymer was obtained. The chamber of the sensor was initially filled with glucose-free polymer solution, while the test cell was filled with PBS buffer, Glucose solution (108 mg/dL) was then introduced into the test cell. The cantilever vibration amplitude, which was proportional to the amplitude of the voltage output of the position sensitive detector, at a fixed frequency (28 Hz) was obtained over time (FIG. 4). It can be seen that the amplitude decreased gradually with time, corresponding to a steady increase in the damping on the cantilever vibration due to glucose binding-induced viscosity increase. The cantilever vibration amplitude finally saturated to a constant level, reflecting that the cantilever vibration had reached steady state and the process of glucose permeation and binding had reached equilibrium. The time constant of this process was determined to be approximately 3 minutes. This is appropriate for CGM applications (Reifman J. et al., J. Diabetes Science & Tech. (2007); 1:478-486), considering from approximately 5 to 15 minutes of response time for commercially available systems and a approximately 5 minutes detection requirement for general clinical treatment.

Figure 5:
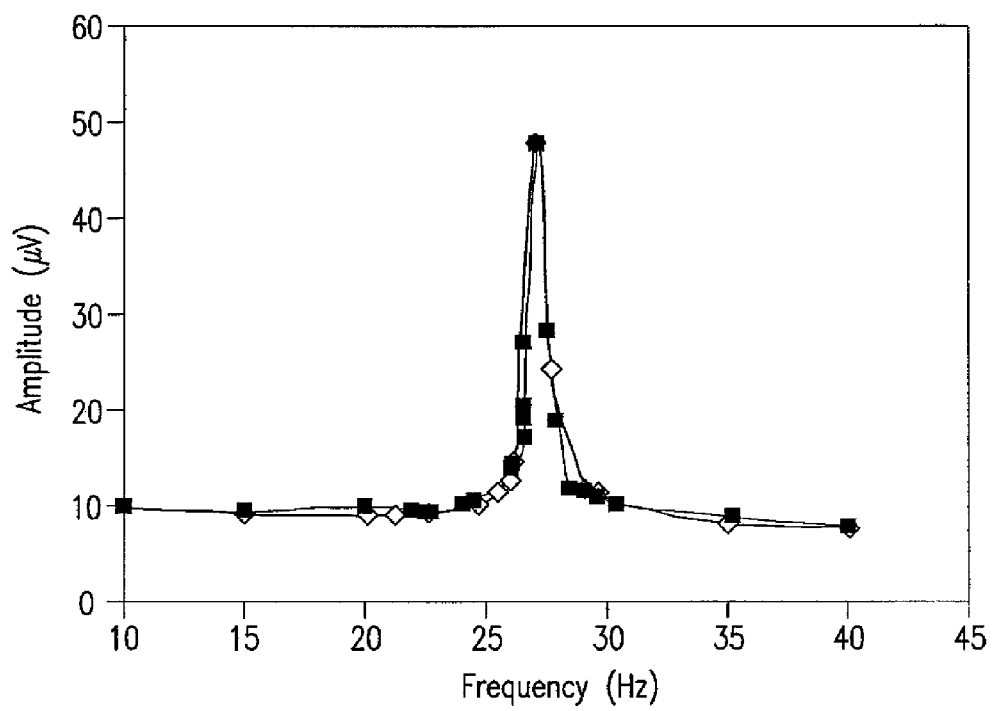
FIG. 5 is a chart illustrating frequency dependent amplitude of the cantilever vibration obtained after glucose permeation and binding had reached equilibrium (squares), as compared to that from a comparison experiment (diamonds) in which glucose concentrations inside and outside the microchamber were pre-equilibrated.

3. Evaluation of Glucose Permeation and Equilibrium Binding Through the Membrane The saturated amplitude frequency response of the cantilever, obtained from the methods above after glucose permeation and binding had reached equilibrium, was compared with results from a comparison experiment. In the comparison experiment, the microchamber and test cell were both filled with a polymer solution that was mixed with glucose at 108 mg/dL. Thus, the glucose concentrations inside and outside the microchamber were pre-equilibrated at the predetermined value. The cantilever vibration amplitude frequency responses obtained from these two experiments are shown in FIG. 5. The responses exhibited resonances at almost identical frequencies (27.0 Hz and 27.2 Hz) with nearly the same amplitudes (48 µV and 47.6 µV). The amplitudes at other frequencies also agree within 6%.

The small discrepancies between the two responses can be attributed to the required separate preparation of the samples used in the two experiments. These experiments confirm that the process of glucose permeation through the membrane and binding to the polymer indeed achieved equilibrium, and the sensor would be capable of accurately determining glucose concentrations in its implanted environment.

4. Steady-State Response at Varying Glucose Concentrations

Figure 6:
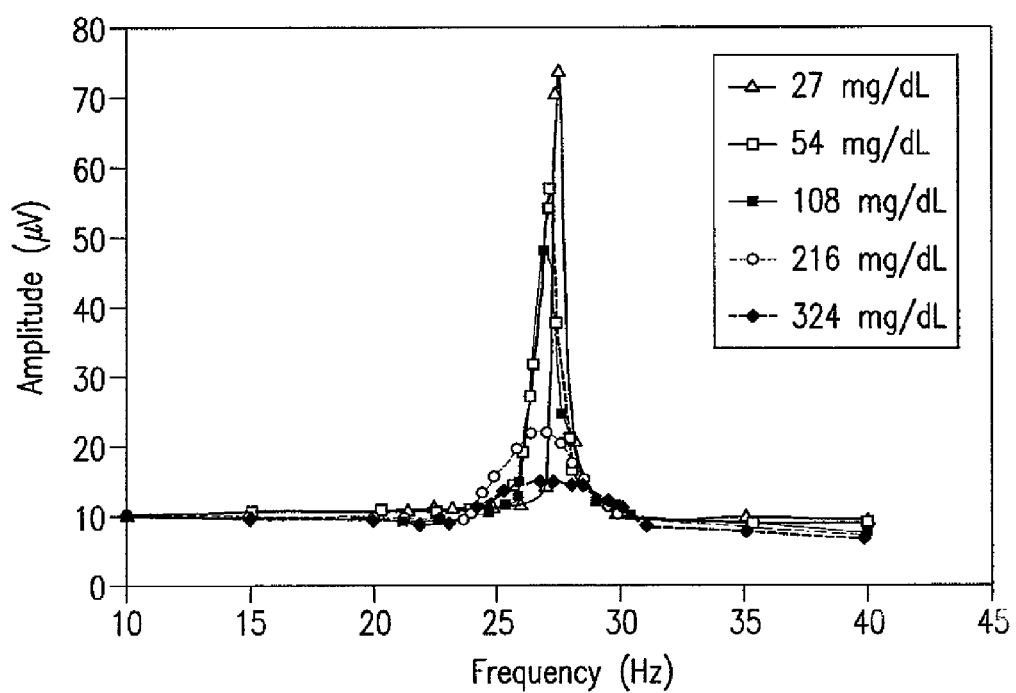
FIG. 6 is a chart illustrating frequency dependent amplitude of the cantilever vibration at physiologically relevant glucose concentrations.
Figure 7:
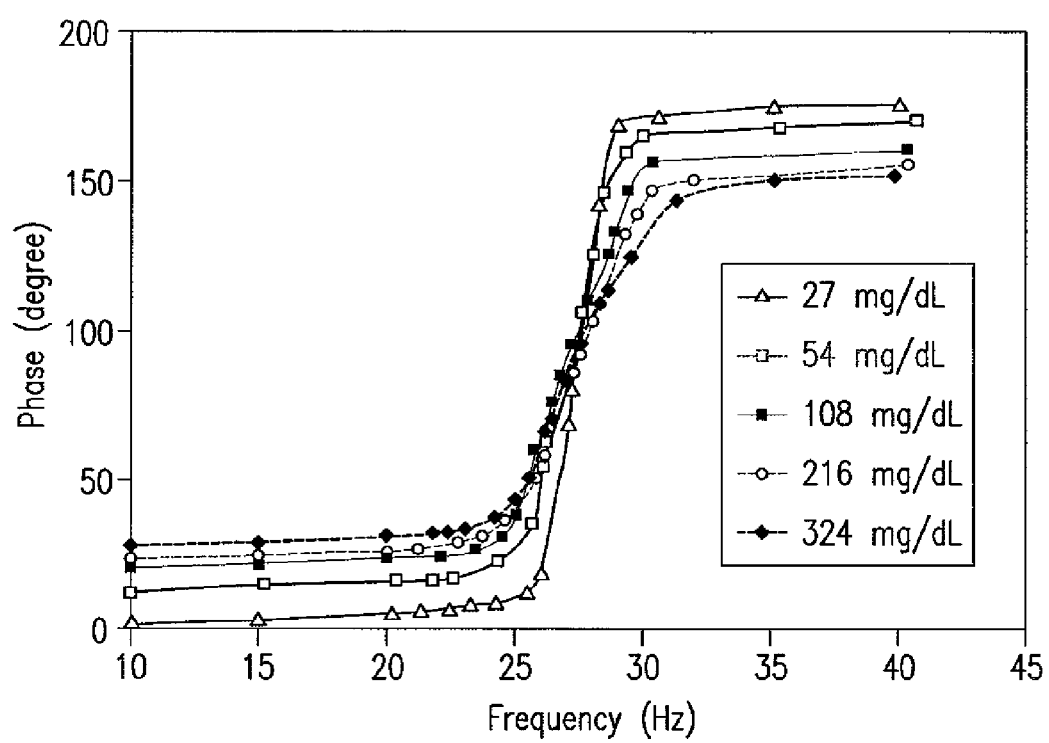
FIG. 7 is a chart illustrating frequency dependent phase lag of the cantilever vibration at physiologically relevant glucose concentrations.

To investigate the dependence of cantilever vibration characteristics on the excitation frequency, the steady-state cantilever vibration was then measured at varying, physiologically relevant glucose concentrations. The vibration exhibited resonance behavior at all glucose concentrations tested (FIGS. 6-7), As the glucose concentration increased from 27 mg/dL to 324 mg/dL, the resonance peak of the vibration amplitude decreased consistently by about 70% (FIG. 6). This was accompanied by a downward shift of the resonance frequency by about 0.77 Hz (from 27.54 to 26.77 Hz, see FIG. 6) and an attenuation of vibration Q-factor from 29 to 7. These observations indicate a significant increase in vibrational damping, which is consistent with increased viscosity of the polymer solution at higher glucose concentrations. In addition, there was a significant change in the phase lag between the cantilever vibration and the magnetic excitation for the cantilever vibration (FIG. 7). For example, at 10 Hz, the phase lag increased from 2.2 degree at 27 mg/dL to 28.3 degree at 324 mg/dL (FIG. 7), and at 15 Hz, the phase shift increased from 4 degree at 27 mg/dL to 30 degree at 324 mg/dL (FIG. 7). Based on the resolution of the phase measurements (0.01 degree), this implies that the sensor would be able to resolve glucose concentrations at about 0.1 mg/dL resolution.

5. Simulated Glucose Variation Measurements

Figure 10:
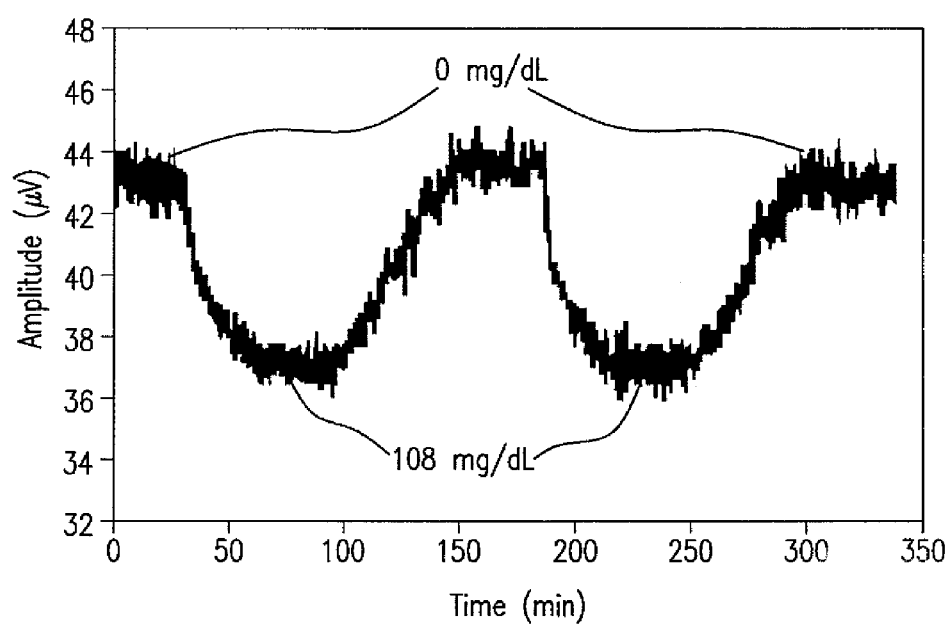
FIG. 10 is a chart illustrating reversibility of the MEMS sensor to glucose concentration changes. The noise shown reflects environmental disturbances to the optical setup.

First, the reversibility of the sensor with respect to glucose concentration changes was tested by alternatively measuring 0 and 108 mg/dL glucose solutions (FIG. 10). The measured vibration amplitude at 28 Hz repeatedly alternated between 37 and 43 µV. Measurements of a time-dependent sequence of glucose variations were made to simulate possible glucose concentration changes in the interstitial fluid of a diabetes patient, and also evaluate the reversibility and stability of the sensor. In these measurements (FIG. 8), while a glucose concentration of 108 mg/dL represented a stable daily glucose level, glucose concentrations of 54 mg/dL and 324 mg/dL were used respectively to simulate glucose levels before and after intake of food. In addition, two intermediate glucose concentrations, 162 mg/dL and 216 mg/dL, were also measured. The measured vibration amplitude at 28 Hz varied from 43 µV at 54 mg/dL to 20 µV at 324 mg/dL, and remained to be 37 µV at 108 mg/dL. Various noise observed in the data is attributable to environmental disturbances to the optical setup. In particular, when the sensor was exposed to a glucose concentration after experiencing another sample that was either higher or lower in concentration, virtually the same amplitude was consistently obtained. For example, the average amplitudes at 108 mg/dL over the two periods, approximately defined by the intervals of [110, 200] and [800, 1100] min, were respectively 36.83 µV and 36.36 µV, which agree within 1.3%. Similarly, the reversibility was within 1.06% and 1.13% for the measurement data at 162 and 216 mg/dL glucose concentrations, respectively. This data indicates an excellent reversibility of the sensor in response to glucose concentration variations, indicating its ability for long-term continuous monitoring of glucose in subcutaneous tissue without need of recalibration.

Figure 8:
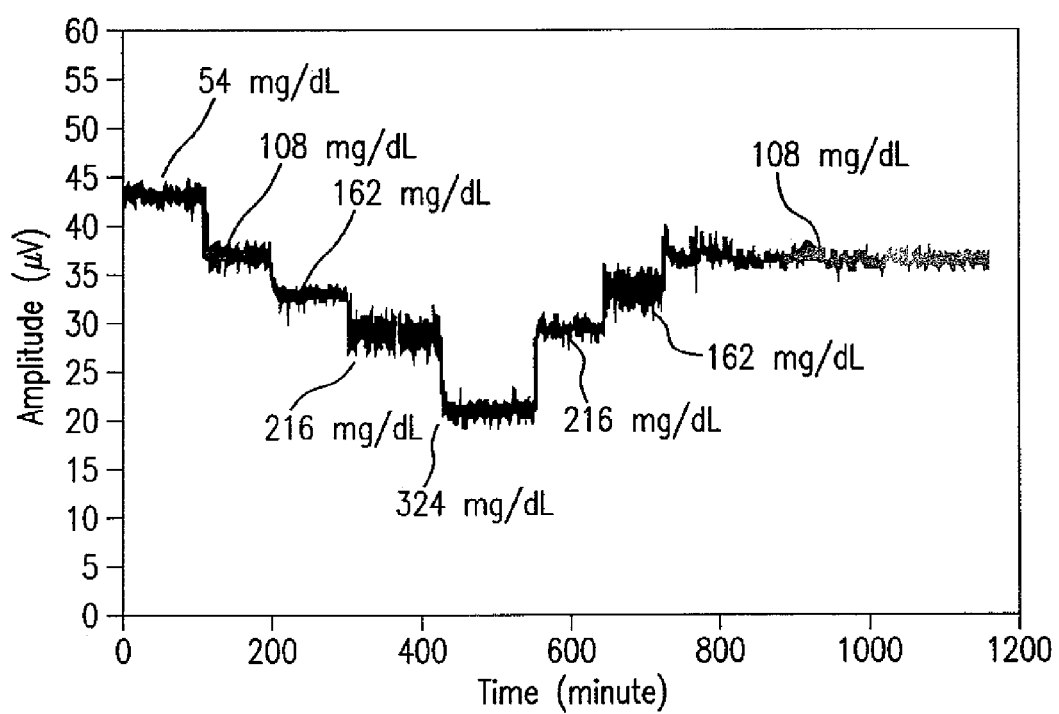
FIG. 8 is a chart illustrating frequency-dependent amplitude of the cantilever vibration in response to a sequence of glucose concentrations.
Figure 11:
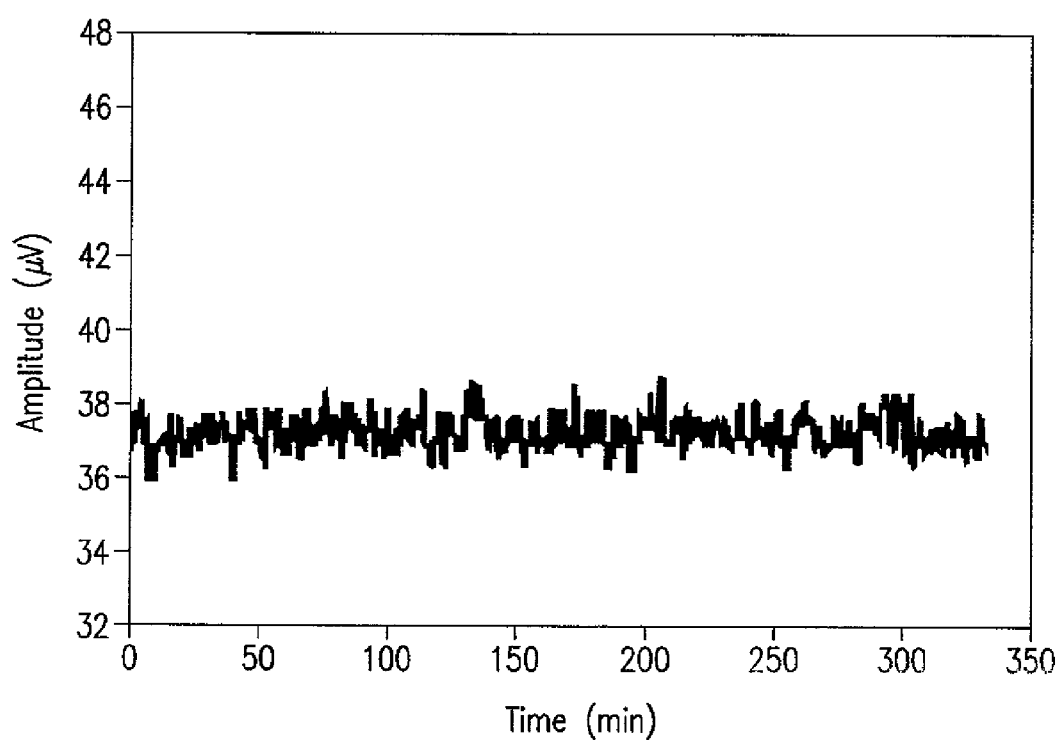
FIG. 11 is a chart illustrating evaluation of drift for the cantilever-based MEMS glucose sensor.

Moreover, the drift in the sensor response was assessed by exposing the sensor to a glucose concentration over an extended period. A consistent vibration amplitude measurement of 37 µV was observed and there was virtually no drift of this measured signal over a preliminary measurement period of 5 hours (FIG. 11). In addition, in the aforementioned experiment as shown in FIG. 8, for the [800, 1100] min period during which the glucose concentration was maintained at 108 mg/dL, the vibration amplitude was steady at 36.36 µV with a standard deviation of 0.427 µV. That is, the drift in the sensor response was about 0.17 µV, or, 0.5% per hour. The drift can be further reduced by minimizing osmotic effects across the membrane, ultimately allow a stability appropriate for long-term continuous glucose monitoring.

Experimental results have shown that this sensor responded to glucose concentration variations at a time scale of approximately 3 minutes which is shorter compared with time responses of commercially available electrochemical CGM sensors. Additionally, comparative experiments confirmed that the process of glucose permeation through the membrane and binding to the polymer was able to equilibrate the glucose concentrations inside and outside the microchamber, making sensor suitable for an implanted setting. Moreover, the sensor response obtained at varying, physiologically relevant glucose concentrations indicated that the sensor was capable of resolving glucose concentration changes by measurement of viscosity. Specifically, over a glucose concentration range of 27-324 mg/dL, the phase frequency response could allow a glucose concentration resolution of 0.1 mg/dL. Finally, the sensor was tested with a time-dependent sequence of glucose variations to simulate possible glucose concentration changes in the interstitial fluid of a diabetes patient. The measurement data indicated that the sensor response was highly reversible (within 1.2%) and stable (within 0.5%/h). These results demonstrate the potential of sensor for use as a subcutaneously implanted device for stable and reliable continuous monitoring of glucose in practical diabetes management.

Example 2

A MEMS Affinity Glucose Sensor Using Permittivity Measurements

In the present example, a sensor using permittivity measurements is used and tested for monitoring the concentration of glucose.

Experimental Method

The disclosed MEMS affinity glucose sensor uses permittivity measurements This sensor employs a biocompatible glucose-specific polymer, PAA-ran-PAAPBA, as the sensing solution. The polymer solution is bound between two parallel-plate electrodes imposed with an AC electric field, which causes the polarization of the polymer manifested as a permittivity. Glucose binding causes the polymer to crosslink, thereby changing the polymer's polarization behavior and hence permittivity. Thus, measuring the capacitance between the electrodes allows determination of glucose concentration. The sensor consists of a pair of parallel-assembled glass coverslips each coated with a thin-film copper electrode. The gap between the electrodes, defined by a photoresist spacer layer, is filled with PAA-ran-PAAPBA solution mixed with glucose, as shown in FIG. 15A.

To fabricate the device, copper electrodes were first deposited and patterned on two glass slides. AZ P4620 photoresist was then spin-coated on both slides to prevent the direct contact between polymer solution and the electrodes. Another photoresist layer was then coated and patterned on one of the glass slide to create a chamber for introduction of the polymer solution. Finally, these two glass slides were aligned and glued together by photoresist reflowing.

Figure 16:
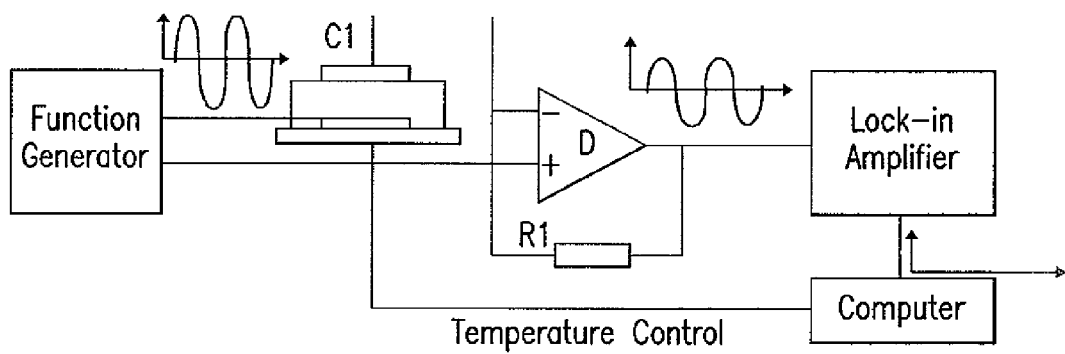
FIG. 16 is a diagram illustrating an experiment setup in accordance with the disclosed subject matter.

The capacitance between the electrodes was measured using a capacitance/voltage transformation circuit (FIG. 16). As shown in FIG. 16, the imaginary part of the output voltage, which was proportional to the polymer solution's complex permittivity, was then obtained. The specificity of device was investigated by measuring polymer solution premixed with glucose and fructose. The device was then characterized by obtaining the frequency-dependent complex permittivity of the polymer solution at various physiological-relevant glucose concentrations. In addition, the device response to glucose solution (free of polymer) was also demonstrated. Finally, the device stability was assessed over an extended measuring period of about 10 hours to evaluate the device's potential suitability for long-term, stable CGM applications.

Results and Discussion

Figure 17:
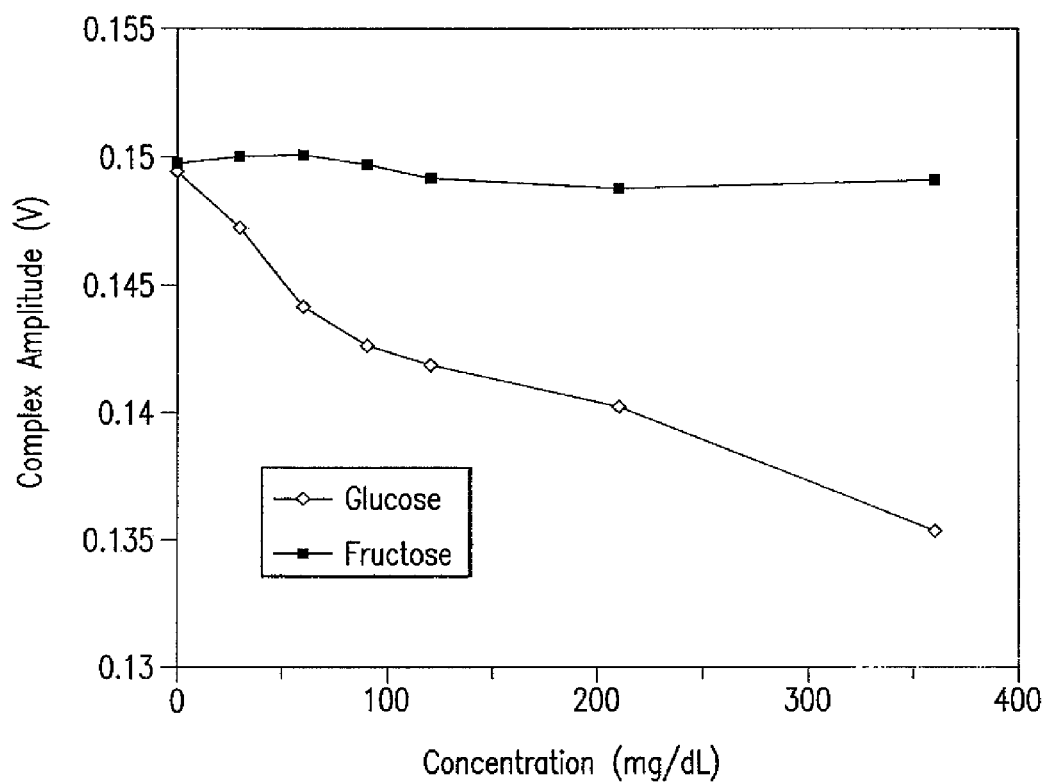
FIG. 17 is a chart illustrating sensor response (at 10 kHz) to polymer solutions at various concentrations of glucose and fructose (an unspecific analyte).
Figure 18:
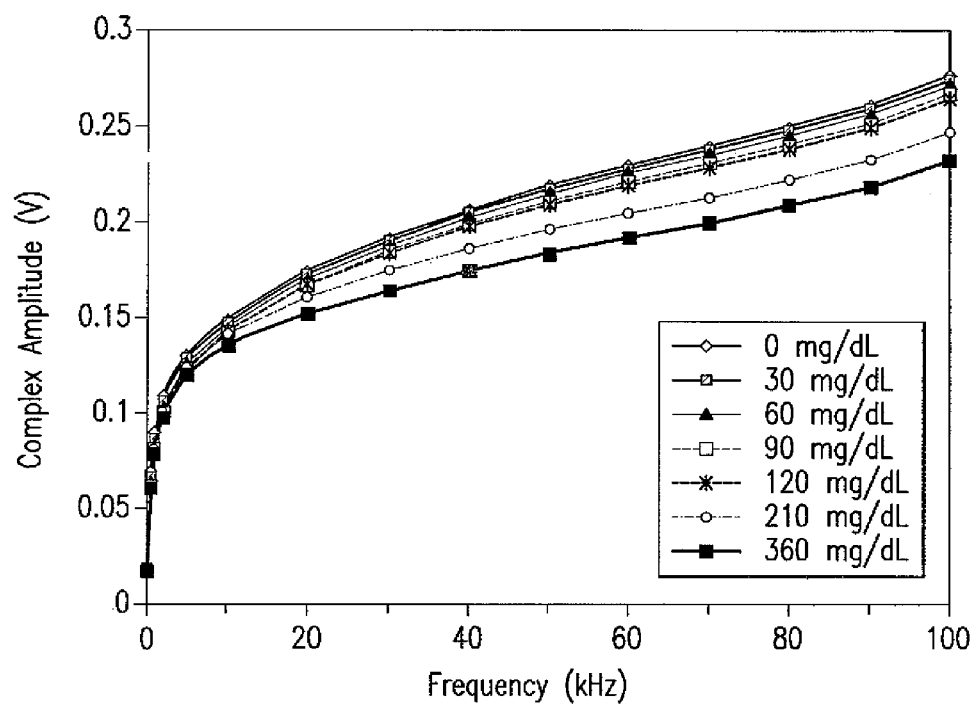
FIG. 18 is a chart illustrating frequency-dependent capacitance changes of the polymer at various glucose concentrations.
Figure 19:
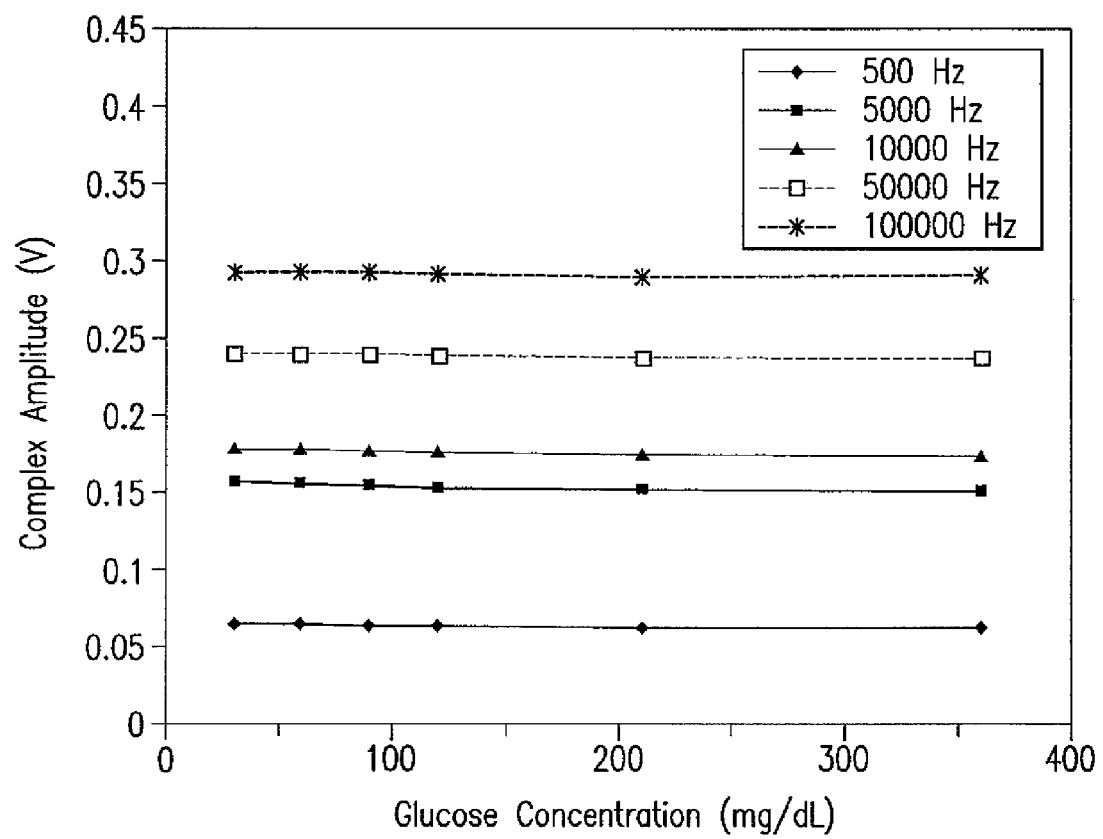
FIG. 19 is a chart illustrating sensor response to pure glucose solutions (free of polymer) at varying glucose concentrations.
Figure 20:
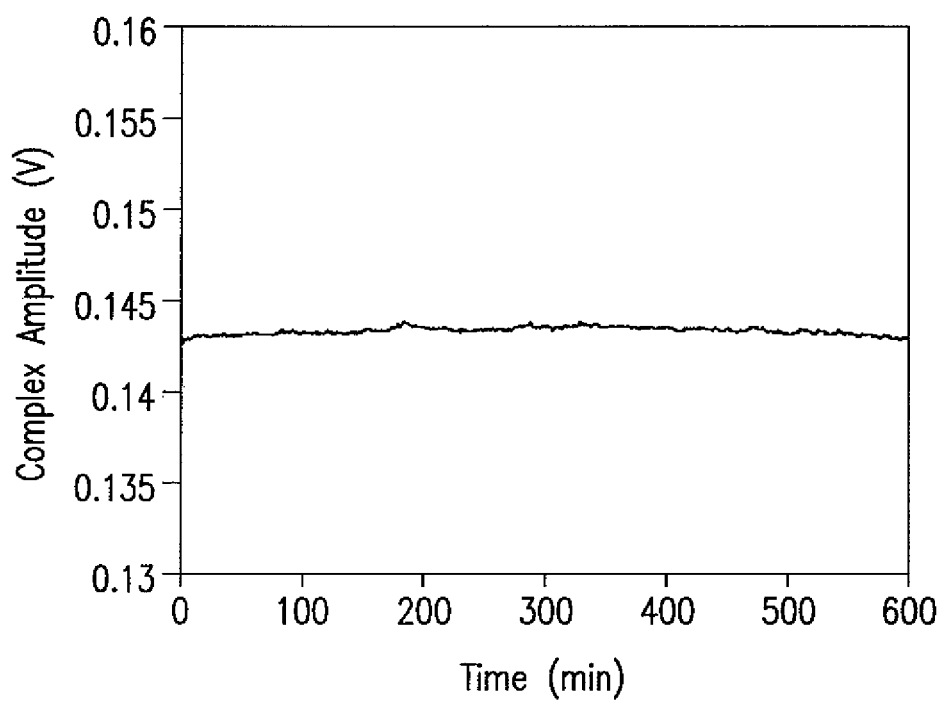
FIG. 20 is a chart illustrating drift of the sensor output (at 10 kHz) over a period of about 10 hours.

First, the device response (at 10 kHz) to varying glucose and fructose concentrations was investigated (FIG. 17). As the glucose concentration varied from 0 to 360 mg/dL, the complex voltage amplitude of the circuit decreased monotonically by 10% from 0.149 to 0.135 V while showing virtually no response to fructose, suggesting glucose-specific detection. Next, the device at additional frequencies was investigated (FIG. 18). Strong frequency dependence of the device complex permittivity was observed, indicating a frequency-dependent polymer polarization. At any given frequency, the imaginary part of the capacitive circuit output consistently decreased with glucose concentration. Measurements with polymer-free glucose solutions showed no response to glucose concentration changes, indicating that the polymer was critical for dielectrically based glucose detection (FIG. 19). Finally, measurements of a polymer solution with 90 mg/dL glucose over 10 hours showed a minimal drift of 9 ppm/hr (FIG. 20), suggesting an excellent stability, ideal for long-term CGM applications.

Example 3

A Capacitive MEMS Viscometric Sensor for Affinity Detection of Glucose

In the present example, a sensor having a vibrational diaphragm is used and tested for monitoring the concentration of glucose.

Experimental Method

Figure 25:
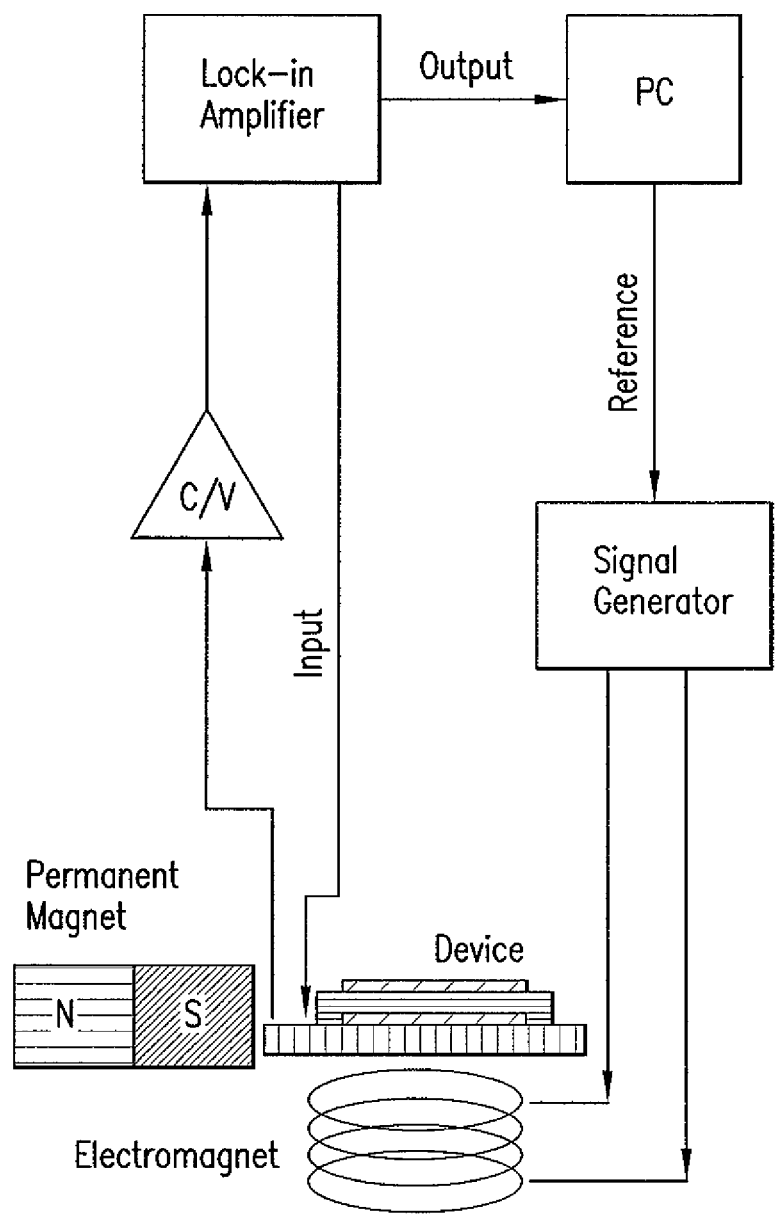
FIG. 25 is a diagram illustrating an experimental setup for characterization of the MEMS glucose sensor.

The sensor consists of a Parylene diaphragm, which vibrates under magnetic excitation inside a microchamber and whose deflection is measured capacitively. The microchamber is filled with a solution of PAA-ran-PAAPBA, and equipped with a cellulose acetate semi-permeable membrane (FIG. 21). The semi-permeable membrane prevents the polymer from escaping while allowing permeation of glucose into and out of the microchamber. Affinity binding between the polymer and glucose results in the crosslinking of the polymer and an increase in the viscosity of the polymer solution. Thus, by measuring the damped diaphragm vibration in the solution, the glucose concentration can be determined. The fabrication process and experimental setup of the sensor are shown in FIGS. 22 and 25, respectively.

The PAA-ran-PAAPBA polymer was synthesized by free radical polymerization (Li S. et al., (2009); Li S. et al., (2008)), and D-(+)-glucose was purchased from Sigma-Aldrich. Phosphate buffer saline (PBS), pH 7.4, was prepared from potassium phosphate (20 mM), NaCl (150 mM) and NaN3 (0.05%). PAA-ran-PAAPBA (284 mg, with 5% of PAAPBA in the polymer) was dissolved in PBS (6 mL) to obtain a solution. Glucose stock solution (1 M) was prepared by dissolving glucose (1.8 g) in PBS to 10 mL. A series of glucose solutions (30 mg/dL, 60 mg/dL, 90 mg/dL, 120 mg/dL, 210 mg/dL, and 360 mg/dL) were prepared by further diluting the stock solution with PBS.

Figure 23:
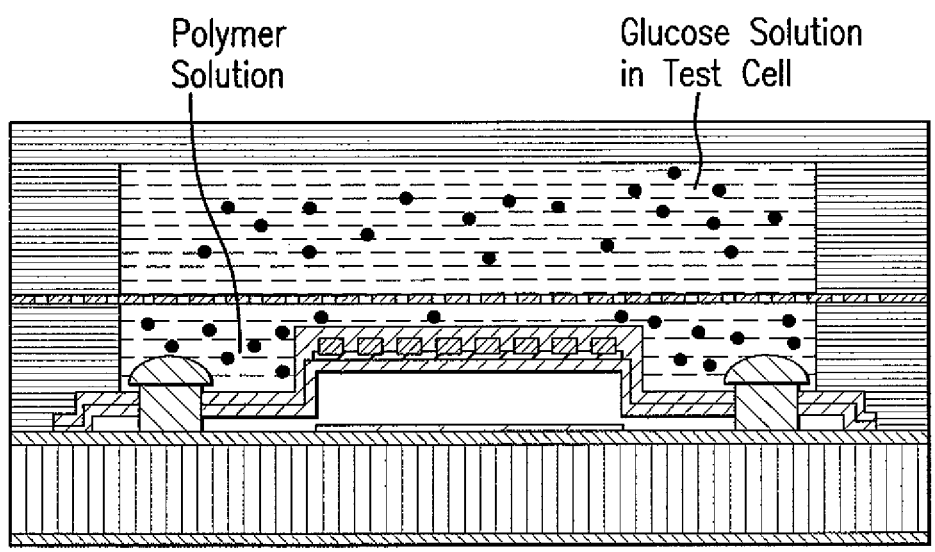
FIG. 23 is a schematic of the sensor outfitted with a flow cell containing glucose solution.

All experiments were conducted at 37° C. with closed-loop temperature control to simulate a physiologically relevant glucose monitoring condition and minimize temperature-dependent viscosity changes. During testing, the sensor's microchamber was filled with an initially glucose-free solution of PAA-ran-PAAPBA (PAAPBA content: 5%). To facilitate experimentation, a test cell (volume: 300 μL) was constructed from a polycarbonate sheet directly above the sensor (FIG. 23). A glucose solution at a given concentration was introduced into the test cell, where it was allowed to permeate through the sensor's semi-permeable membrane to interact with PAA-ran-PAAPBA in the microchamber. Because the volume of the test cell was 30 times that of the microchamber, it was reasonably assumed that the glucose concentration inside the microchamber equalized to the given glucose concentration in the test cell when the glucose permeation reached an equilibrium.

Figure 24:
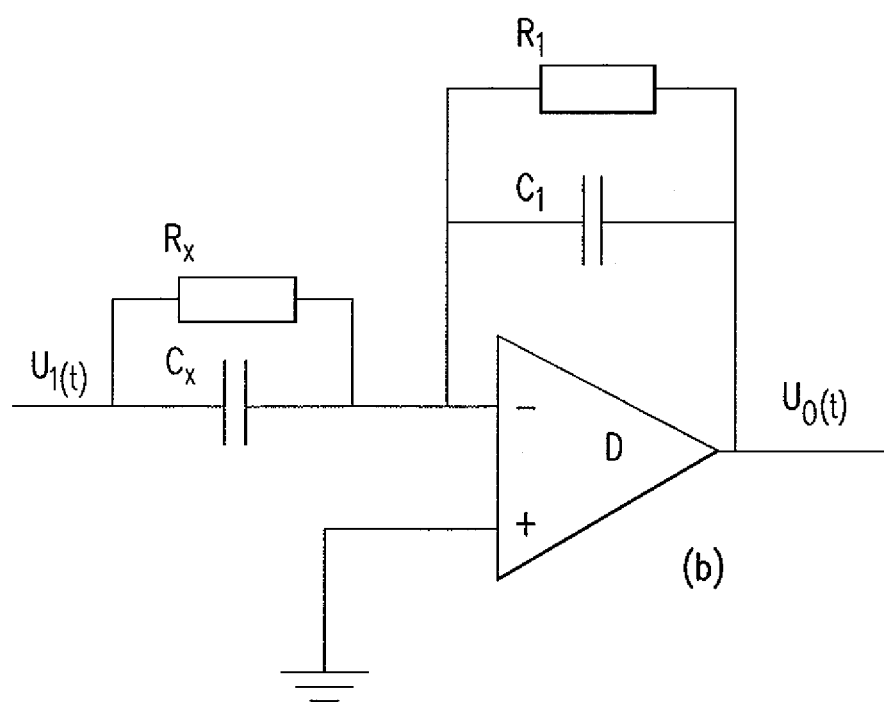
FIG. 24 is a diagram illustrating exemplary capacitive measurement circuitry.

The sensor capacitance was measured using a capacitance-voltage transformation circuit (FIG. 24). Given an input sinusoidal wave, $U_i$ (1 $V_{rms}$), the output voltage, $U_0$, had an amplitude that was proportional to the ratio of the sensor capacitance, $C_x$, to the standard reference capacitance, $C_f$. This output was captured by a lock-in amplifier and acquired by a personal computer. In the experimental setup (FIG. 25), the diaphragm vibration was driven by a home-made solenoid (400 turns of a 250 μm diameter copper wire on a plastic core), which, under a driving voltage of 10 $V_{pp}$, produced a magnetic field strength of about 950 μm at 1000 Hz perpendicular to the cantilever surface. A permanent magnet bar with a field strength of approximately 200 kA/m was placed parallel to the permalloy strips to yield saturated magnetization of the permalloy. A fabricated, not yet packaged sensor is shown in FIG. 13A, while a packaged sensor in the experimental setup is shown in FIG. 13B.

Results and Discussion

The sensor's vibration characteristics at physiologically relevant glucose concentrations under various excitation frequencies were evaluated, and then the observed characteristics with a simplified oscillator model were analyzed. The temporal course of the diaphragm vibrations due to changes in glucose concentration was observed to determine the sensor's response time and its reversibility. Finally, the drift in the sensor response in glucose measurements over an extended measuring period was investigated to evaluate the sensor's potential suitability for long-term, stable CGM applications.

1. Measured Diaphragm Vibration Characteristics

Figure 26A:
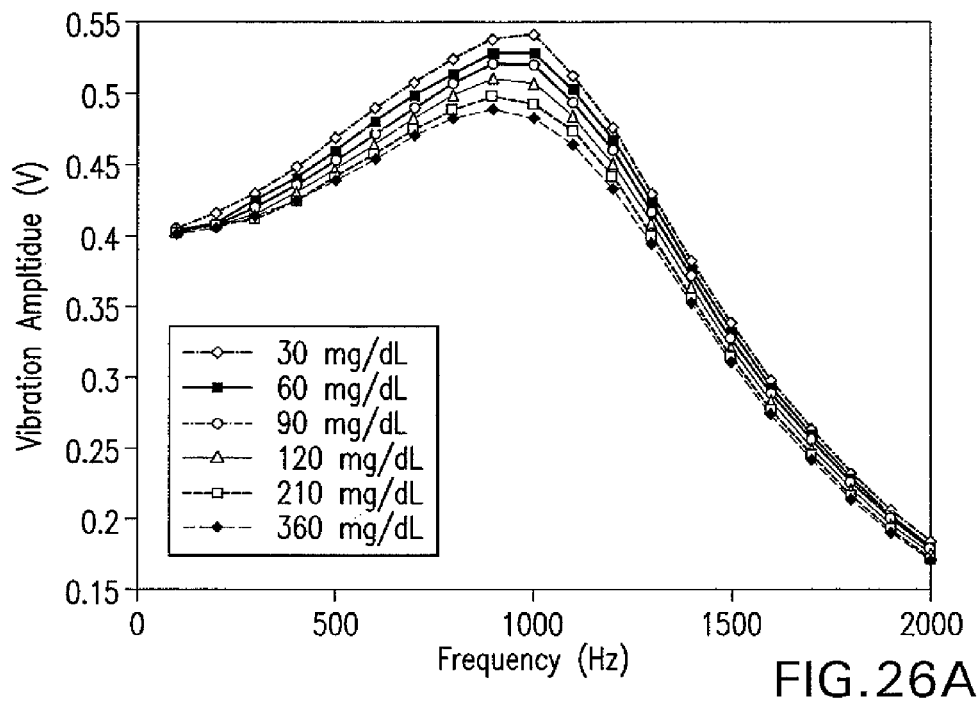
FIGS. 26A-B are a chart illustrating frequency-dependent behavior of the harmonically driven vibration of the sensor diaphragm at physiologically relevant glucose concentrations: (A) amplitude, and (b) phase shift.

The dependence of vibration characteristics of the sensor diaphragm on the excitation frequency was first characterized. In the experiment, the glucose concentration was first allowed to be equilibrated at a physiologically relevant value (30, 60, 90, 120, 210, or 360 mg/dL). The diaphragm vibrated under the excitation of a harmonically time-varying magnetic field, which had a frequency-independent amplitude of approximately 110 A/m. The steady-state amplitude and phase of the diaphragm vibration as a function of the excitation frequency were obtained in terms of the output voltage of the capacitive measurement circuit (FIG. 27). As shown in amplitude frequency response (FIG. 26A), the diaphragm vibration exhibited resonance behavior at all glucose concentrations tested. The resonance peaks were relatively broad because of significant damping from the highly viscous polymer solution. As the glucose concentration increased from 30 to 360 mg/dL, the resonance peak decreased consistently by 53 mV (from 542 to 489 mV). This was accompanied by a downward shift of the resonance frequency by 100 Hz (from 1000 to 900 Hz). These observations indicate a significant increase in vibrational damping, which is consistent with the increased viscosity of the polymer solution at higher glucose concentrations.

Figure 26B:
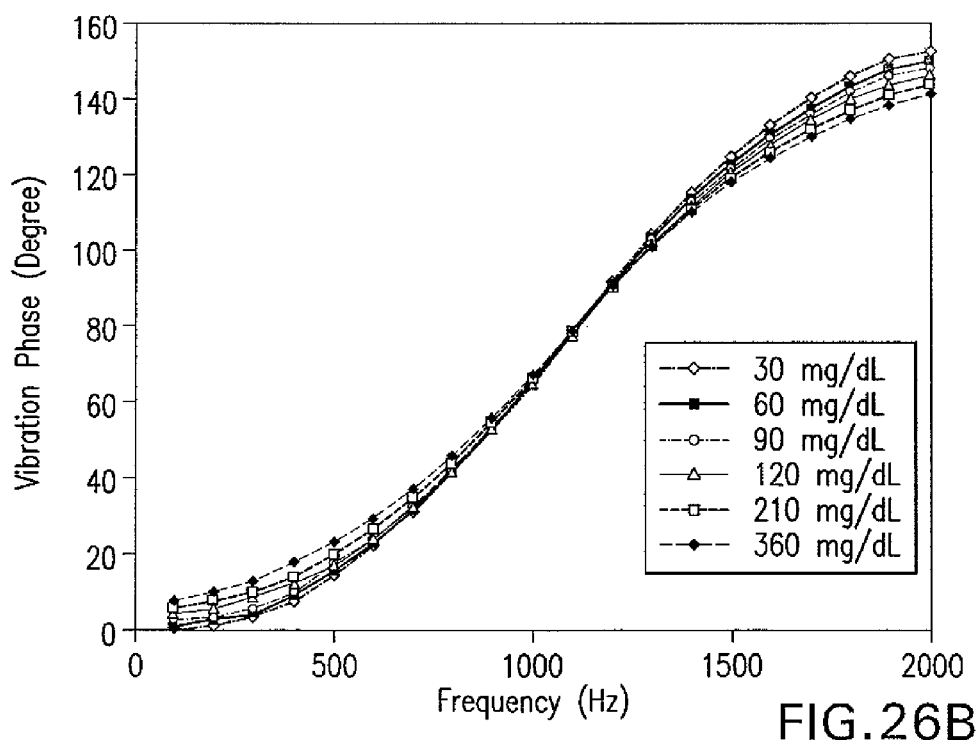

In addition, from the phase frequency response (FIG. 26B), it can be seen that at a given frequency, there was a significant change in the phase shift between the diaphragm vibration and the magnetic excitation. For example, at 400 Hz, the phase shift decreased from 17.68 degree at 30 mg/dL to 7.69 degree at 360 mg/dL, which agrees with increased damping at higher glucose concentrations. The phase shift curves at the different glucose concentrations intersect at a single frequency of approximately 1200 Hz, at which the phase shift was 91.8 degree. This is consistent with the behavior of a single-degree-of-freedom damped harmonic oscillator, and suggests that the natural frequency of the diaphragm, taking into account the added mass from the polymer solution, was about 1200 Hz.

2. Time-Resolved Measurements of Sensor Response to Glucose Concentration Changes Having systematically characterized the diaphragm vibration characteristics, time-resolved measurements of the diaphragm vibration in response to glucose concentration changes were performed, and these measurements were applied to assess the response time, reversibility and drift in the sensor response.

To characterize the sensor response time, the glucose concentration was initially allowed to be equilibrated at 90 mg/dL in the test cell and microchamber. Next, the solution in the test cell was replaced with another glucose solution at 120 mg/dL. When the glucose concentration inside the microchamber had equilibrated to 120 mg/dL, the reverse process was initiated, in which the test cell was refilled with a 90 mg/dL glucose concentration. Some of the polymer-bound glucose molecules dissociated and permeated out of the semipermeable membrane, allowing the glucose concentration inside the microchamber to equilibrate to 90 mg/dL. The process of solution refilling of the test cell lasted about 10 seconds, which was sufficiently fast when compared with the glucose concentration equilibration. During the equilibration processes, the harmonic vibration of the diaphragm, at a fixed frequency of 1000 Hz, was measured as a function of time. A fixed frequency is used for a much larger excitation magnetic field amplitude (250 A/m) than that used above (110 A/m) when the frequency was varied, which was limited by the frequency-dependence of the magnetic field generated by the voltage-controlled solenoid.

Figure 29:
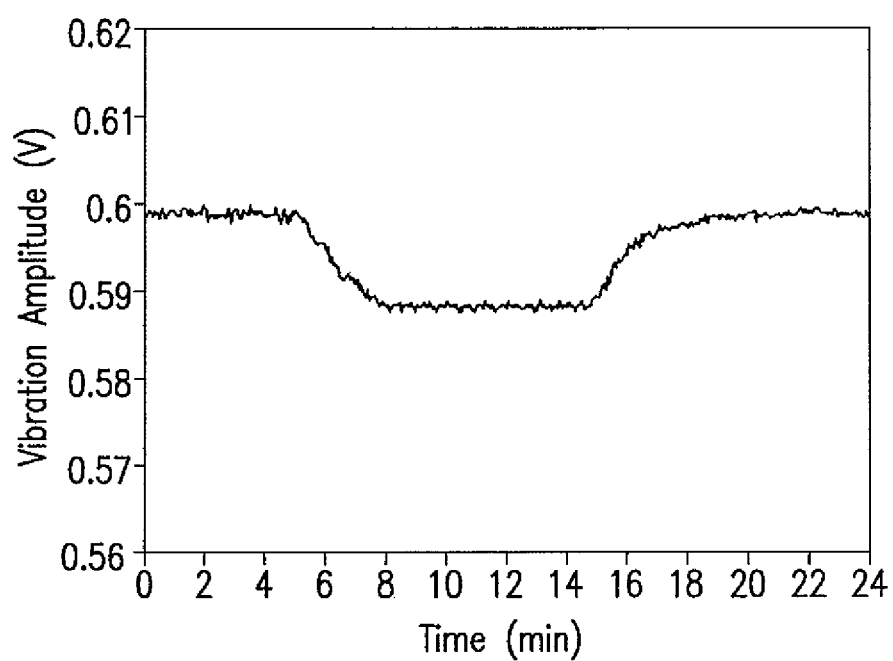
FIG. 29 is a chart illustrating time course of the diaphragm vibration amplitude at 1000 Hz as the sensor responded to glucose concentration changes from 90 to 120 mg/dL, which was then reversed to 90 mg/dL.

As shown in FIG. 29, while the glucose concentration varied from 90 to 120 mg/dL, the diaphragm vibration amplitude decreased with time, corresponding to increased damping on the diaphragm vibration due to glucose binding-induced viscosity increase. The vibration amplitude finally saturated to a constant level, reflecting that the process of glucose permeation and binding had reached a dynamic equilibrium. The time constant of this process was determined to be approximately 1.5 minutes. In the reverse process where the glucose concentration in the test cell was decreased from 120 mg/dL to 90 mg/dL, the vibration amplitude increased with time due to reduced viscous damping from the polymer solution. The time constant for the reverse process was approximately 1.7 minutes. The longer reverse time constant could be due to the smaller diffusivity of glucose molecules in the initially more viscous polymer solution and needs to be investigated in future work. Note that these time constants compare favorably with response times of commercially available systems that range from 5 to 15 minutes ("MiniMed Paradigm® REAL-Time Insulin Pump and Continuous Glucose Monitoring System," http://www.minimed.com/products/insulinpumps/index.html; "FreeStyle Navigator® Continuous Glucose Monitoring System," http://www.abbottdiabetescare.com; "DexCom™ STS® System," http://www.dexcom.com), and can be further reduced by shortening the distance between the semi-permeable membrane and the diaphragm. Thus, the experimentally determined glucose response time constants (approximately 1.5 and approximately 1.7 minutes) are considerably shorter than a theoretically estimated time constant (approximately 6 minutes), which does not yet include the time taking by glucose-polymer binding kinetics. This suggests that the sensor exhibited a faster response time than theoretically expected. It was conjectured that this was caused by the possible active mixing of glucose in the chamber as induced by the diaphragm vibration, which could also have induced the vibration of the semi-permeable membrane by fluid-structure interactions.

The reversibility of the sensor response, which can be obtained by comparing differences in sensor output between two separated measurements at the same glucose concentration were also assessed. For example, as shown in FIG. 29, the sensor output at 1000 Hz varied from 0.598 (averaged over the period [0, 5] minutes) to 0.588 V (averaged over [9, 14]

minutes) as the glucose concentration varied from 90 to 120 mg/dL. The sensor output then returned to 0.598 V (averaged over [19, 24] minutes) when the glucose concentration was reversed to 90 mg/dL. The difference between the average sensor outputs over the two periods with the glucose concentration at 90 mg/dL was only about 0.3 mV, or 60 ppm. Thus, there is excellent reversibility in the sensor with respect to glucose concentration variations.

In general, the measurement accuracy of the sensor is primarily determined by three factors. That is, in addition to reversibility considerations above, the sensor accuracy is also limited by the repeatability of the sensor output from multiple measurements at a certain glucose concentration, and the noise in the measurement as the glucose concentration is held constant. In terms of repeatability, for example, multiple measurements of glucose samples at 90 mg/dL at 1000 Hz were performed, and the measurements resulted in the sensor output differing by only about 90 ppm. The accuracy was more significantly influenced by the measurement noise, which can be observed in FIGS. 29-30. This noise is attributed to randomly present tiny air bubbles in the polymer solution that influenced the diaphragm vibration, as well as small temperature fluctuations in the chamber due to limitations in temperature control. The noise, characterized by standard deviations from FIG. 29, was about 0.32 mV, or 3% of the sensor output change (10.7 mV) as the glucose concentration was varied from 90 to 120 mg/dL. This translates into a glucose measurement resolution of about 1.8 mg/dL at 90 mg/dL, which is considered excellent in the context of practical applications.

Figure 30:
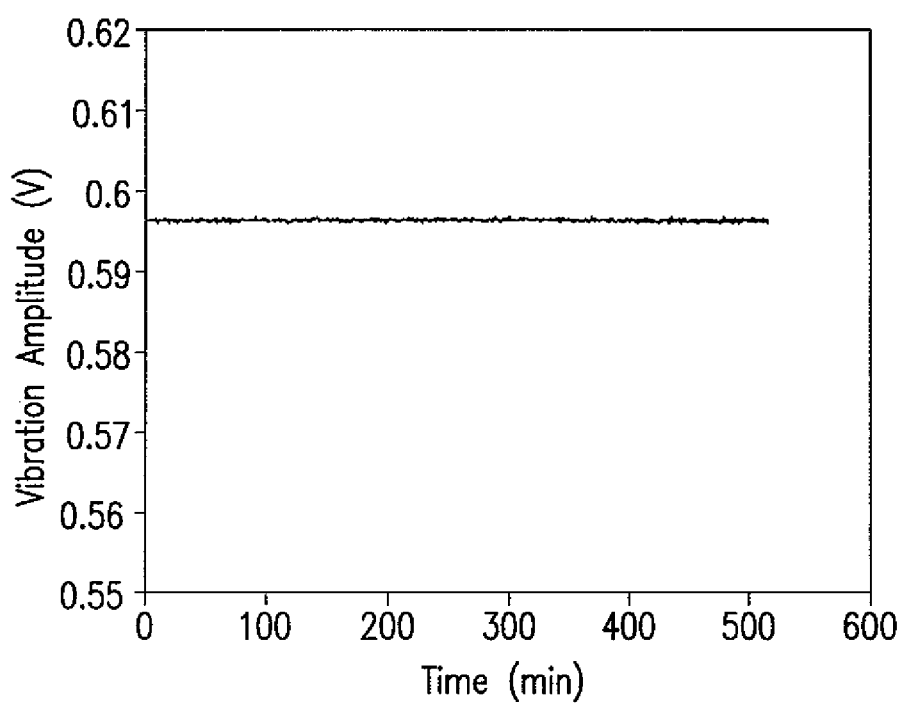
FIG. 30 is a chart illustrating diaphragm vibration amplitude a5 1000 Hz over an extended time duration as the glucose concentration was held constant at 90 mg/dL.

Finally, the drift of the sensor output by exposing it to constant glucose concentrations over long periods was studied. For example, the harmonic vibration amplitude at 1000 Hz as the glucose concentration was held constant at 90 mg/dL (FIG. 30). It can be seen that the sensor output was steady at 0.596 V over a period of about 10 hours, with a drift rate of less than 10 μV/hr. The drift can be further reduced by measures such as minimization of osmotic effects across the membrane, optimization of the parameters in closed-loop temperature control, and development of improved capacitance measurement circuitry. The low drift demonstrates that the sensor holds potential to offer highly stable measurements for long-term continuous glucose monitoring.

The MEMS sensor vibration characteristics obtained at several selected glucose concentrations indicated that the sensor was capable of resolving glucose concentration changes by viscosity measurements. By fitting the experimental data to a simple 1-DOF mass-spring-damper model, the sensor's natural frequency was estimated to be 1190 Hz, while the dimensionless damping ratio increased from 0.37 to 0.44 as the glucose concentration varied from 30 to 360 mg/dL, reflecting the steady increase of the viscosity of the polymer solution with glucose concentration. Experimental results have also shown that the sensor responded quite rapidly to glucose concentration variations with a time constant of approximately 1.5 minutes which is shorter than the time responses of commercially available electrochemical CGM sensors. Additionally, it was also observed from the experimental data that the sensor response to glucose concentration changes was highly reversible; for example, as the glucose concentration was changed from 90 to 120 mg/dL and then reversed 90 mg/dL, the deviation in the diaphragm vibration amplitude was only 60 ppm. Finally, it was demonstrated that the sensor response was highly stable. For example, as the glucose concentration was held constant at 90 mg/dL, the drift rate in the diaphragm vibration amplitude was only 0.17 ppm/hr. These results demonstrate that the sensor holds the potential to be used as a subcutaneously implanted device for long-term, stable and reliable continuous monitoring of glucose in practical diabetes management.

Example 4

MEMS-Based Dielectric Affinity Biosensing

In the present example, a sensor using permittivity measurements is used and tested for monitoring the concentration of glucose.

Experimental Methods and Materials

The sensor consists of a microchamber 50 filled with an aqueous solution of PAA-ran-PAAPBA, mixed with glucose at physiologically relevant concentrations. Two gold electrodes deposited on the top 51 and bottom 52 chamber walls were patterned to the chamber shape and dimensions. A gold thin-film temperature sensor 53 was also integrated on the bottom chamber wall. An AC electromagnetic (EM) field imposed on the electrodes caused the polarization of the polymer polarization, which was directly depended on glucose binding (FIGS. 32A-C). Thus, the permittivity can be obtained to determine the glucose concentration.

To fabricate the device, a gold thin film 100 nm thick was deposited by thermal evaporation and pattered to form the electrodes (each 1×1 mm$^2$ in area) on the top and bottom glass slides, as well as the temperature sensor (280×200 μm$^2$ in area, and 40 μm in line width) on the bottom slide. Thereafter, passivation photoresist layers (500 nm in thickness) were spin-coated on the glass slides to prevent the direct contact of the electrodes with the PAA-ran-PAAPBA dielectric solution. Another photoresist layer 55 (thickness: 3 μm) was then deposited and patterned on the bottom glass slide to define the microchamber (over a 1.5×1.5 mm$^2$ area on the slide) along with an inlet and an outlet for introduction and removal of the polymer solution. The top glass slide was next placed over the bottom slide and aligned to form the microchamber along with a parallel-plate capacitor comprised of the two electrodes. The photoresist layers were finally baked at 180° C. for 10 minutes on a hotplate, causing the reflow of the photoresist and bonding of the glass slides to complete the device fabrication. Images of a fabricated device before and after packaging are shown in FIGS. 32B and C.

Figure 33A:
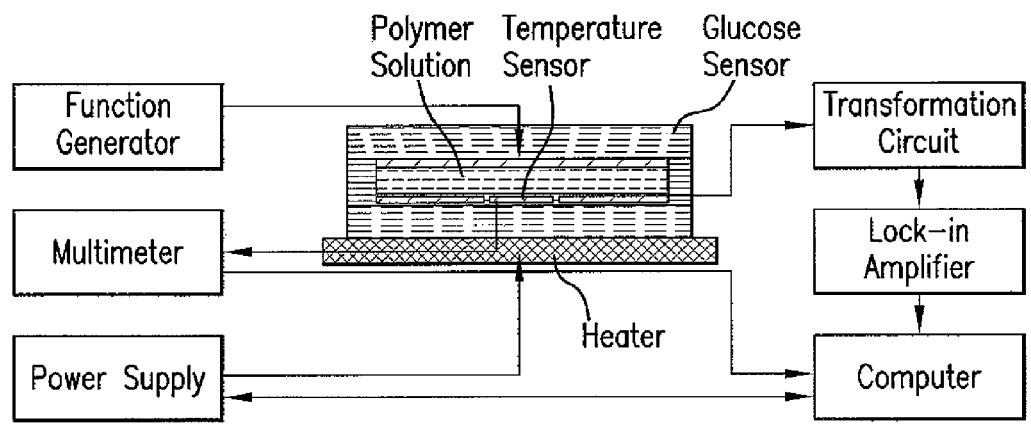
FIGS. 33A-B depict an experimental setup (a). The equivalent capacitance of the device is measured by a transformation circuit. (b) The output voltage of the capacitance/voltage transformation circuit is proportional to the sensor admittance.
Figure 33B:
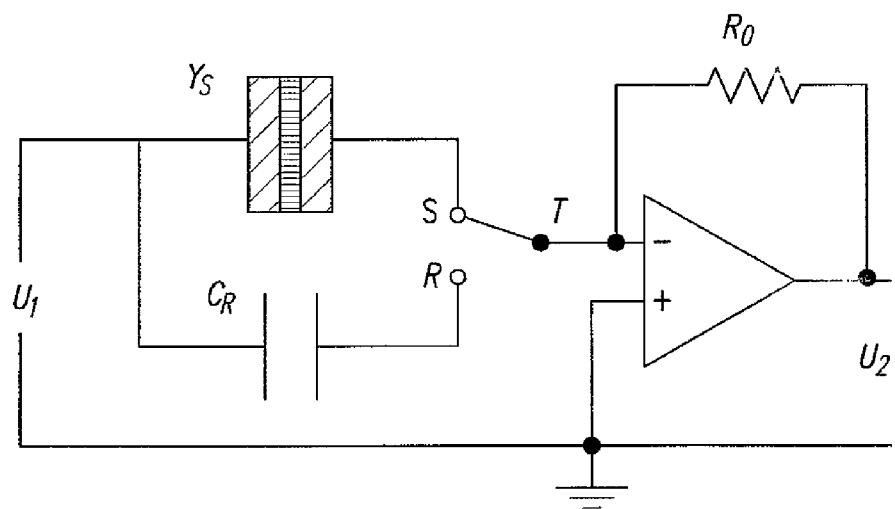

The sensor was filled with a sample consisting of the polymer solution mixed with glucose at varying concentrations, and measured as shown in FIG. 33A. The temperature of the device was fixed at 37° C. using closed-loop control, in which the device was heated by a Peltier heater (Melcor, CP14) according to feedback from the integrated temperature sensor. The sensor was coupled to a capacitance/voltage transformation circuit (FIG. 33B) driven by a sinusoidal input of angular frequency ω=2πf from a function generator (Agilent, 33220A). All experiments were conducted at frequencies up to 100 kHz as allowed by the lock-in amplifier. When the device was inserted into the circuit (with the switch "T" connected to the position "S" in FIG. 33B), an input voltage $U_{1S}e^{j\omega t}$ from the function generator yielded an output voltage $U_{2S}e^{j\omega t}$ which was measured using a lock-in amplifier (Stanford Research Systems, SR844). This was immediately followed by switching the terminal "T" to a reference capacitor $C_R$ (position "R" in FIG. 33B), with an input voltage $U_{1R}e^{j\omega t}$ yielding an output voltage $U_{2R}e^{j\omega t}$ measured similarly. These allowed the determination of the device's complex admittance as follows:

$$Y_S = G_S + j\omega C_S = j\omega C_R (U_{2S}^* U_{1R}^*)/(U_{1S}^* U_{2R}) \qquad (6)$$

where $C_S$ and $G_S$ are the equivalent capacitance and conductance, respectively.

PAA-ran-PAAPBA polymers with varying compositions were synthesized by free radical polymerization (Li S et al., (2008). Three polymer compositions, respectively with an acrylamide (AA) to 3-acrylamidophenylboronic acid (AAPBA) molar ratio of 50, 20 and 12.5 (or approximately 2%, 5% and 7% in PAAPBA content) were used in the experiments. Corresponding to these compositions, the polymers had molecular weights of 176,800, 170,700 and 71,700 Da, respectively. To prepare solutions of the polymers, 284 mg of each polymer was dissolved separately in 6 mL of phosphate buffered saline (PBS). The PBS buffer (pH 7.4) was prepared from potassium phosphate (20 mM), NaCl (150 mM) and $NaN_3$ (0.05%). D-(+)-glucose, D-(+)-galactose and D-fructose, used respectively as target and interfering sugars during dielectric affinity detection, were purchased from Sigma-Aldrich. Glucose stock solution (1 M) was prepared by dissolving glucose (1.8 g) in PBS to 10 mL. A series of polymer solutions mixed with glucose at varying concentrations (30, 60, 90, 120, 210, and 360 mg/dL) were prepared. Polymer solutions were also mixed with galactose and fructose.

Results

Figure 34A:
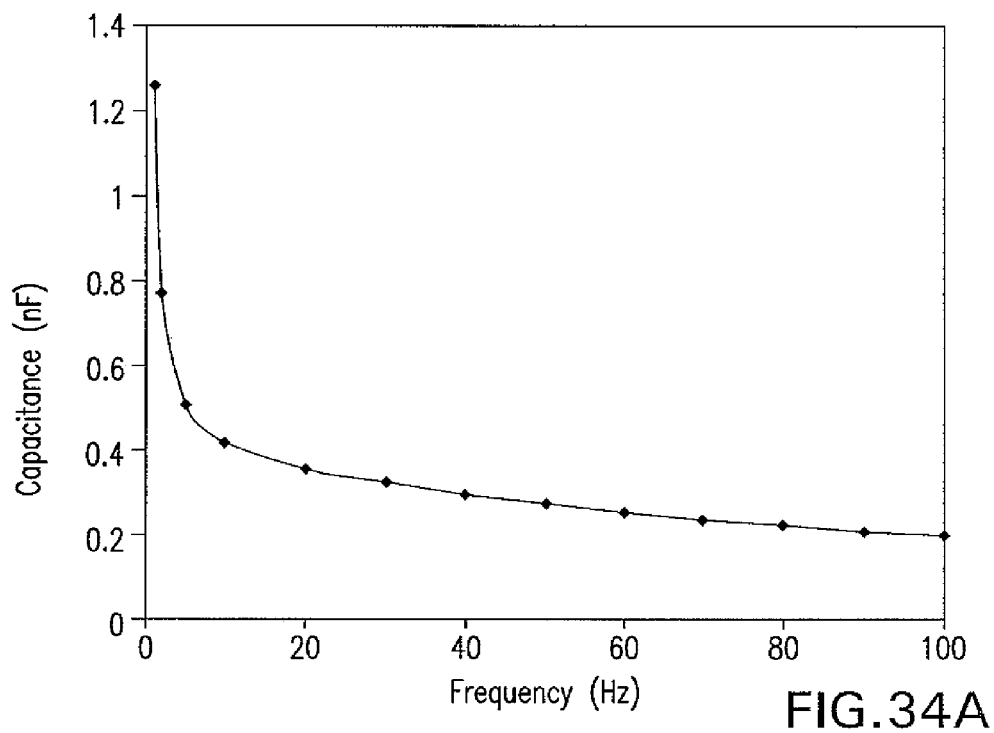
FIGS. 34A-B depict frequency dependence of the equivalent device capacitance (PAAPBA content of the PAA-ran-PAAPBA polymer: 5%). (a) Equivalent capacitance when the polymer solution is free of glucose. (b) Changes in equivalent capacitance at physiologically relevant glucose concentrations with respect to the glucose-free case.
Figure 34B:
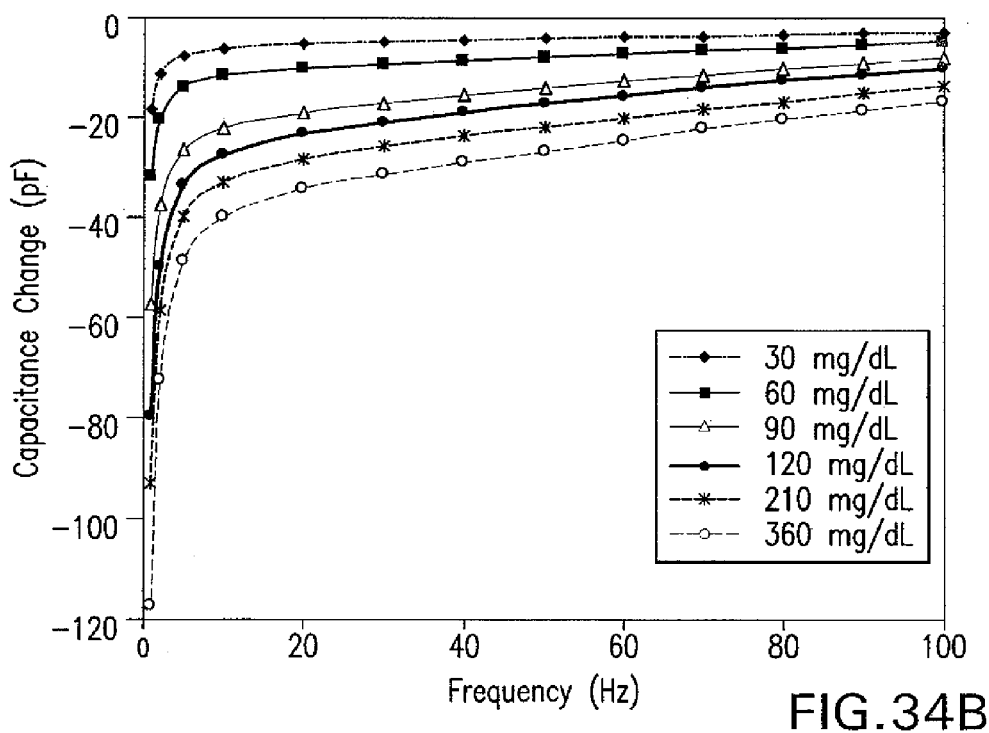

Regarding the device response to varying glucose concentrations at frequencies from 1 to 100 kHz, the microchamber was filled with a polymer solution premixed with glucose at physiologically relevant concentrations. The device's equivalent capacitance as a function of frequency is shown in FIGS. 34A and B for a typical PAA-ran-PAAPBA polymer composition, which had a PAAPBA content of 5%. The sensor capacitance decreased consistently with the frequency (FIG. 34A), showing a relaxation of the polymer solution's dielectric behavior (below). In addition, at a given frequency, the sensor capacitance decreased consistently with increasing glucose concentration (FIG. 34B). The permittivity of the solution decreases due to the binding of the polymer with glucose. In addition, given the voltage measurement resolution of the experimental setup (~70 µV), the data is used along with a differential form of Eq. (6) to determine that the device is capable of resolving glucose concentration changes down to 0.5 mg/dL, which would be sufficiently accurate for practical continuous glucose monitoring applications.

Figure 35:
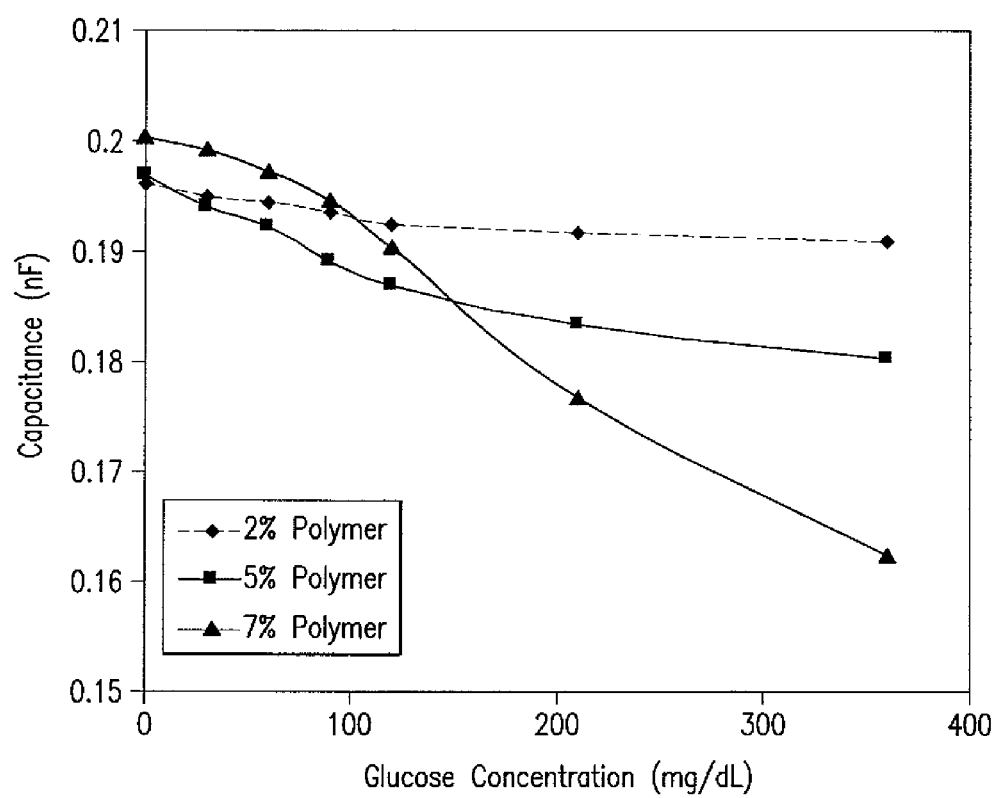
FIG. 35 shows the equivalent capacitance of a device at 100 kHz plotted as a function of glucose concentration for different polymer compositions.

The dependence of the measured equivalent capacitance on glucose concentration at a fixed frequency (100 kHz) when the device was filled with PAA-ran-PAAPBA polymers with different PAAPBA contents (2%, 5% and 7%) is shown in FIG. 35. In the absence of glucose, the equivalent capacitance increased with the PAAPBA content of the polymer. Additionally, a higher PAAPBA content offers a higher sensitivity of the equivalent capacitance, and hence the solution permittivity, to the glucose concentration.

The polymers with 2% and 5% PAAPBA contents were more sensitive at the low glucose concentrations, while showing a somewhat saturated response as the glucose concentration increased. The polymer with 7% PAAPBA content was highly sensitive at the elevated glucose concentrations, although there was a significance decrease in sensitivity at the low end of the glucose concentration range tested. This significantly different trend can be attributable to a transition from a liquid state to a gel-like structure of the 7%-PAAPBA polymer solution at elevated glucose concentrations, a phenomenon not observed for the other polymer compositions.

Figure 36:
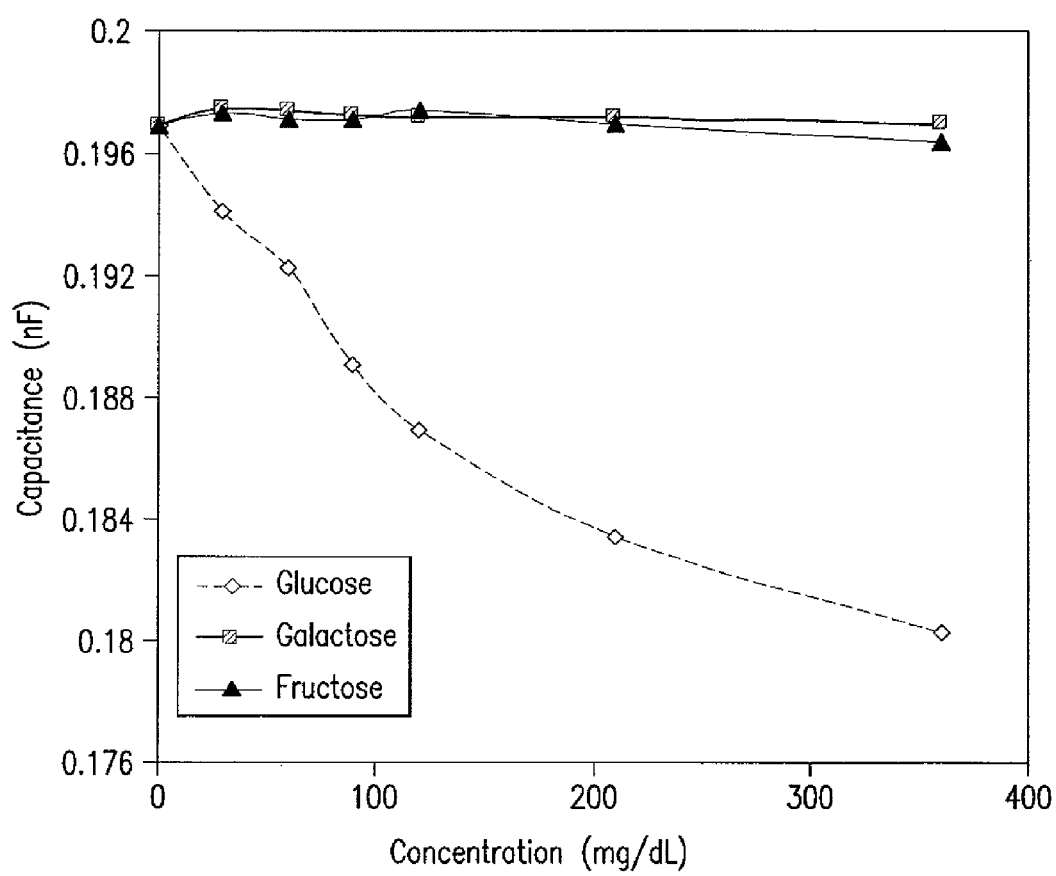
FIG. 36 shows equivalent capacitance at 100 kHz plotted as a function of concentrations of glucose, and the unspecific monosaccharides galactose and fructose.

To investigate the specificity of the device to glucose, the device filled with a 5%-PAAPBA polymer was tested with unspecific monosaccharides such as fructose and galactose (FIG. 36), which represented potential interferents with glucose measurements. In all concentrations tested, the device responses to fructose and galactose were less than 0.4% and 5% of the device response to glucose. These unspecific responses can be considered negligible, given that fructose and galactose exist in interstitial fluid at concentrations about 1000 times lower than glucose. These results show that the dielectrically based affinity glucose sensing approach can be highly specific.

The foregoing merely illustrates the principles of the disclosed subject matter. Various modifications and alterations to the described embodiments will be apparent to those skilled in the art in view of the inventors' teachings herein. Features of existing methods can be seamlessly integrated into the methods of the exemplary embodiments of the disclosed subject matter or a similar method. It will thus be appreciated that those skilled in the art will be able to devise numerous methods which, although not explicitly shown or described herein, embody the principles of the disclosed subject matter and are thus within its spirit and scope.

Patents, patent applications, publications, procedures, and the like are cited throughout this application, the disclosures of which are incorporated herein by reference in their entireties.

What is claimed is:

1. A sensor for monitoring a target analyte by using a polymer solution that is capable of binding to the analyte, comprising
    (a) a semi-permeable membrane comprising a material permeable to the analyte;
    (b) a substrate; and
    (c) a microchamber including a vibrational diaphragm having a periphery formed between the semi-permeable membrane and the substrate, and adapted to receive the polymer solution, such that when the analyte is placed on the semi-permeable membrane, at least a portion of the analyte will permeate through the semi-permeable membrane and bind to at least a portion of the polymer solution to thereby cause a change in vibration of the vibrational diaphragm,
        wherein the vibrational diaphragm is attached to the substrate around the entire periphery of the vibrational diaphragm.

2. the sensor of claim 1, wherein the change in vibration of the vibrational diaphragm is caused by a change in viscosity of the polymer solution.

3. the sensor of claim 1, wherein the polymer comprises a polymer that reversely binds to the analyte.

4. The sensor of claim 1, wherein the analyte comprises glucose.

5. The sensor of claim 1, wherein the polymer comprises a plurality of boronic acid moieties.

6. The sensor of claim 5, wherein the polymer comprises poly(acrylamide-ran-3-acrylamidophenylboronic acid).

7. The sensor of claim 1, wherein the vibrational diaphragm is fabricated from Parylene.

8. The sensor of claim 1, further comprising a top electrode embedded in the vibrational diaphragm within the micro chamber to thereby form a capacitor with a bottom electrode on the substrate.

9. The sensor of claim 8, wherein the capacitor is adapted to sense a change in the capacitance between the top electrode and the bottom electrode caused by binding between the analyte and the polymer.

10. The sensor of claim 1, wherein the vibrational diaphragm further comprises at least one integrated permalloy film.

11. The sensor of claim 10, wherein the permalloy film further comprises a Parylene layer for passivation.

* * * * *